(12) United States Patent
Elvig et al.

(10) Patent No.: US 8,765,199 B2
(45) Date of Patent: Jul. 1, 2014

(54) MASHING PROCESS

(75) Inventors: Niels Elvig, Holte (DK); Per Linaa Joergensen, Copenhagen (DK); Michael Thomas, Davis, CA (US)

(73) Assignees: Novozymes A/S, Bagsvaerd (DK); Novozymes Inc., Davis, CA (US)

( * ) Notice: Subject to any disclaimer, the term of this patent is extended or adjusted under 35 U.S.C. 154(b) by 909 days.

(21) Appl. No.: 12/326,326

(22) Filed: Dec. 2, 2008

(65) Prior Publication Data

US 2009/0142447 A1    Jun. 4, 2009

Related U.S. Application Data

(63) Continuation of application No. PCT/US2007/087209, filed on Dec. 12, 2007, and a continuation-in-part of application No. PCT/EP2007/055863, filed on Jun. 14, 2007.

(60) Provisional application No. 60/813,944, filed on Jun. 15, 2006.

(51) Int. Cl.
*C12C 3/00* (2006.01)

(52) U.S. Cl.
USPC .................. 426/13; 426/16; 426/592; 426/64

(58) Field of Classification Search
USPC .................. 426/13, 16, 592, 64; 435/210
See application file for complete search history.

(56) References Cited

U.S. PATENT DOCUMENTS

| | | | |
|---|---|---|---|
| 3,081,172 A | 3/1963 | Dennis et al. | |
| 4,318,927 A | 3/1982 | Marshall | |
| 4,355,047 A * | 10/1982 | Line et al. | 426/13 |
| 4,528,198 A | 7/1985 | Mizerak et al. | |
| 4,560,651 A | 12/1985 | Nielsen | |
| 4,666,718 A | 5/1987 | Lowery et al. | |
| 5,736,375 A | 4/1998 | Deweer | |
| 2006/0057684 A1 | 3/2006 | Bisgaard-Frantzen | |

FOREIGN PATENT DOCUMENTS

| | | |
|---|---|---|
| EP | 1063285 A1 | 12/2000 |
| GB | 2056484 | 3/1981 |
| GB | 2069527 | 8/1981 |
| JP | 2004-173533 | 6/2004 |
| JP | 2004173533 | 6/2004 |
| WO | 99/01543 A1 | 1/1999 |
| WO | 99/49011 A1 | 9/1999 |
| WO | WO 99/45124 | 9/1999 |
| WO | WO 00/01796 | 1/2000 |
| WO | WO 01/51620 | 7/2001 |
| WO | 02/092741 A2 | 11/2002 |
| WO | WO 03/062409 | 7/2003 |
| WO | WO 2004/011591 | 2/2004 |
| WO | 2004/080923 A2 | 9/2004 |
| WO | WO2004/080923 A2 | 9/2004 |
| WO | 2005/059084 A1 | 6/2005 |
| WO | WO 2005/059084 A1 | 6/2005 |
| WO | WO 2005/121305 | 12/2005 |
| WO | 2007/000011 A1 | 1/2007 |
| WO | WO 2007/000011 A1 | 1/2007 |
| WO | WO 2007/113292 | 10/2007 |
| WO | WO 2007/144393 | 12/2007 |
| ZA | 1998-03237 | 4/1998 |
| ZA | 19980323 | 4/1998 |

OTHER PUBLICATIONS

Sequence search results—Run on Sep. 7, 2011.*
Adrian et al, FEMS Microbiology Letters, vol. 115, No. 1, pp. 97-106 (1994).
Willox, I. C. et al, Master Brewers Association of the Americas, vol. 14, No. 2, pp. 105-110 (1977).
Wieg et al, Process Biochemistry, vol. 4, No. 5, pp. 33-38 (1969).
Anonymous, Brewing Industry Products, Grama Trading Ltd, 1-3 (2003).
Anonymous, Handbuch—Abstract (2003).
Anonymous, Handbuch, Forschung.Oekolandbau.DE, pp. 1-42 (2003).
Goode et al, MBAA TQ, vol. 42, No. 3, pp. 184-198 (2005).
Odibo et al, Mircen J, vol. 5, No. 2, pp. 187-192 (1989).
Wieg et al, Process Biochem, pp. 46-48 (1970).
Genbank Access No. AAP04499 (2003) pp. 2.
Genbank Access No. CAC28076 (2006) pp. 2.
Anonymous, Handbuch zur Kontrolle des GVO-Verbotes im Ökologischen Landbau gemäss VO(EWG) Nr. 2092/91, pp. 1-42 (2003).
Broll, Summary of Project sponsored by German Federal Programme for Organic Agriculture (2003).
Goode et al., MBAA TQ, vol. 42, No. 3, pp. 184-198 (2005).
Grama Trading Ltd., Brewing Industry Products (2003).
Odibo et al., MIRCEN Journal, vol. 5, No. 2, pp. 187-192 (1989).
Wieg, Brewing Science, pp. 533-571 (1987).
Wieg et al., Process Biochemistry, pp. 46-48 (1970).
Kelly et al, —EBI, Access No. Z22515 (1993).
Kelly et al, FEMS Microbiol Lett, vol. 115, No. 1, pp. 97-106 (1994).

* cited by examiner

*Primary Examiner* — D. Lawrence Tarazano
*Assistant Examiner* — Hamid R Badr
(74) *Attorney, Agent, or Firm* — Kristin J. McNamara

(57) ABSTRACT

The present invention provides processes for producing a brewers wort comprising forming a mash from a grist, and contacting said mash with a pullulanase.

12 Claims, No Drawings

MASHING PROCESS

CROSS-REFERENCE TO RELATED APPLICATIONS

This application is a continuation of international application no. PCT/US2007/87209 filed Dec. 12, 2007 and is a continuation-in-part of international application no. PCT/EP2007/055863 filed Jun. 14, 2007 which claims priority or the benefit under 35 U.S.C. 119 of U.S. provisional application No. 60/813,944 filed Jun. 15, 2006, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to an improved mashing process for production of a brewer's wort and for production of a beer.

BACKGROUND OF THE INVENTION

In modern mashing processes, enzymes are often added as a supplement when mashing malt is low in enzymes or to allow use of all adjunct grists. Enzymes may also be applied in mashing of well modified malts with high enzyme content in order to increase the extract recovery as well as the amount of fermentable sugars. It is thus well known to apply debranching enzymes, e.g., isoamylase or pullulanase to increase the yield fermentable sugars. Debranching enzymes may be applied in processes for production of low calorie beer. Such processes are the subject of Willox et al. (MBAA Technical Quarterly, 1977, 14: 105), U.S. Pat. Nos. 4,528,198, 4,666,718, and 4,318,927, and GB 2056484 and GB 2069527.

SUMMARY OF THE INVENTION

The present inventors have now surprisingly discovered that by using a certain pullulanase, mashing can be achieved using a smaller amount of enzyme protein.

Accordingly, in a first aspect the invention provides a process for producing a brewers wort comprising forming a mash from a grist, and contacting said mash with a pullulanase (E.C. 3.2.1.41), wherein said pullulanase has an amino acid sequence which a) is at least 50% identical to the amino acid sequence shown in SEQ ID NO: 4, or b) is encoded by a nucleic acid sequence which hybridizes under low stringency conditions with i) a complementary strand of a nucleic acid sequence encoding the amino acid sequence shown in SEQ ID NO: 4, or ii) a subsequence of (i) of at least 100 nucleotides.

In a second aspect the invention provides a wort produced by the process of the first aspect.

In a third aspect the invention provides concentrated and/or dried wort produced by the process of the first aspect.

In a fourth aspect the invention provides beer produced from the wort of the second and third aspect.

In a fifth aspect the invention provides a composition suitable for use in the process of the first aspect, said composition comprising pullulanase (E.C. 3.2.1.41), glucoamylase and optionally alpha-amylase, wherein the pullulanase has an amino acid sequence which a) is at least 50% identical to the amino acid sequence shown in SEQ ID NO: 4, or b) is encoded by a nucleic acid sequence which hybridizes under low stringency conditions with i) a complementary strand of a nucleic acid sequence encoding the amino acid sequence shown in SEQ ID NO: 4, or ii) a subsequence of (i) of at least 100 nucleotides.

DETAILED DESCRIPTION OF THE INVENTION

Brewing processes are well-known in the art, and generally involve the steps of malting, mashing, and fermentation. Mashing is the process of converting starch from the milled barley malt and solid adjuncts into fermentable and unfermentable sugars to produce wort of the desired composition. Traditional mashing involves mixing milled barley malt and adjuncts with water at a set temperature and volume to continue the biochemical changes initiated during the malting process. The mashing process is conducted over a period of time at various temperatures in order to activate the endogenous enzymes responsible for the degradation of proteins and carbohydrates. By far the most important change brought about in mashing is the conversion of starch molecules into fermentable sugars. The principal enzymes responsible for starch conversion in a traditional mashing process are alpha- and beta-amylases. Alpha-amylase very rapidly reduces insoluble and soluble starch by splitting starch molecules into many shorter chains that can be attacked by beta-amylase. The disaccharide produced is maltose. In addition to the maltose formed during mashing short branched glucose oligomers are produced. The short branched glucose oligomers are non fermentable sugars and add to the taste as well as the amount of calories of the finished beer.

After mashing, when all the starch has been broken down, it is necessary to separate the liquid extract (the wort) from the solids (spent grains). Wort separation, lautering, is important because the solids contain large amounts of protein, poorly modified starch, fatty material, silicates, and polyphenols (tannins). Following the separation of the wort from the spent grains the wort may be fermented with brewers yeast to produce a beer.

Further information on conventional brewing processes may be found in "Technology Brewing and Malting" by Wolfgang Kunze of the Research and Teaching Institute of Brewing, Berlin (VLB), 2nd revised Edition 1999, ISBN 3-921690-39-0.

The short branched glucose oligomers formed during mashing may be further hydrolyzed by addition of exogenous enzymes (enzymes added in addition to the malt). Debranching enzymes such as pullulanase and isoamylase hydrolyze the branching alpha-1-6 glucosidic bonds in these oligomers, thereby releasing glucose or maltose and straight-chained oligomers which are subject to the action of endogenous (malt derived) and/or exogenous enzymes, e.g., alpha-amylases, beta-amylases and glucoamylases.

The present invention provides a new process suitable for producing a wort that is low in non-fermentable sugars. The process applies an expressly selected pullulanase activity.

Definitions

Throughout this disclosure, various terms that are generally understood by those of ordinary skill in the arts, are used. Several terms are used with specific meaning, as defined below.

As used herein the term "grist" is understood as the starch or sugar containing material that is the basis for beer production, e.g., the barley malt and the adjunct. Generally, the grist does not contain any added water.

The term "malt" is understood as any malted cereal grain, in particular barley.

The term "adjunct" is understood as the part of the grist which is not barley malt. The adjunct may comprise any starch rich plant material, e.g., unmalted grain, such as barley, rice, corn, wheat, rye, sorghum and readily fermentable sugar and/or syrup.

The term "mash" is understood as a starch containing slurry comprising grist steeped in water.

The term "wort" is understood as the unfermented liquor run-off following extracting the grist during mashing.

The term "spent grains" is understood as the drained solids remaining when the grist has been extracted and the wort separated.

The term "beer" is understood as fermented wort, i.e., an alcoholic beverage brewed from barley malt, optionally adjunct and hops.

The term "homologous sequence" is used to characterize a sequence having an amino acid sequence that is at least 70%, preferably at least 75%, or at least 80%, or at least 85%, or 90%, or at least 95%, at least 96%, at least 97%, at least 98% at least 99% or even at least 100% identical to a known sequence. The relevant part of the amino acid sequence for the homology determination is the mature polypeptide, i.e., without the signal peptide. The term "homologous sequence" is also used to characterize DNA sequences which hybridize at low stringency, medium stringency, medium/high stringency, high stringency, or even very high stringency with a known sequence. Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al., 1989) for 10 min, and pre-hybridization of the filter in a solution of 5×SSC, 5×Denhardt's solution (Sambrook et al., 1989), 0.5% SDS and 100 micrograms/ml of denatured sonicated salmon sperm DNA (Sambrook et al., 1989), followed by hybridization in the same solution containing a concentration of 10 ng/ml of a random-primed (Feinberg and Vogelstein, 1983, *Anal. Biochem.* 132:6-13), 32P-dCTP-labeled (specific activity>1× 109 cpm/microgram) probe for 12 hours at about 45° C. The filter is then washed twice for 30 minutes in 2×SSC, 0.5% SDS at about 55° C. (low stringency), more preferably at about 60° C. (medium stringency), still more preferably at about 65° C. (medium/high stringency), even more preferably at about 70° C. (high stringency), and even more preferably at about 75° C. (very high stringency). Molecules to which the oligonucleotide probe hybridizes under these conditions are detected using an x-ray film.

The term "identity" when used about polypeptide or DNA sequences and referred to in this disclosure is understood as the degree of identity between two sequences indicating a derivation of the first sequence from the second. The identity may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman and Wunsch, 1970, *Journal of Molecular Biology* 48: 443-453. The following settings for polypeptide sequence comparison are used: GAP creation penalty of 3.0 and GAP extension penalty of 0.1. The degree of identity between an amino acid sequence of the present invention and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

Wort Production

In accordance with the first aspect the invention provides a process for producing a brewer's wort comprising forming a mash from a grist, and contacting said mash with a pullulanase (E.C. 3.2.1.41), wherein said pullulanase has an amino acid sequence which a) is at least 50%, at least 60%, at least 70%, at least 75%, at least 80%, or at least 85%, or 90%, or at least 95%, at least 96%, at least 97%, at least 98% or even at least 99% identical to the amino acid sequence shown in SEQ ID NO: 4, or b) is encoded by a nucleic acid sequence which hybridizes under low stringency, medium stringency, medium/high stringency, high stringency, or even very high stringency with i) a complementary strand of a nucleic acid sequence encoding the amino acid sequence shown in SEQ ID NO: 4, or ii) a subsequence of (i) of at least 100 nucleotides, at least 200 nucleotides, at least 300 nucleotides, at least 500 nucleotides, at least 1000 nucleotides, or even at least 1500 nucleotides. In a preferred embodiment, the pullulanase has an amino acid sequence which differs by no more than 100 amino acids, preferably by no more than 80 amino acids, more preferred by no more than 50 amino acids, more preferably by no more than 30 amino acids, even more preferably by no more than 20 amino acids, and most preferably by no more than 10 amino acids from the amino acid sequence of SEQ ID NO: 3.

The grist of the first aspect comprises starch containing malted grain and/or adjunct. The grist may preferably comprise from 0% to 100%, preferably from 20% to 100%, preferably from 30% to 100%, more preferably from 40% to 100%, even more preferably from 50% to 100%, yet more preferably from 60% to 100%, such as from 80% to 100% or even most preferably from 90% to 100% adjunct, unmalted grain and/or unmalted barley. In a particular embodiment the adjunct is composed of 100% unmalted barley. Furthermore, the grist preferably comprises from 0% to 100%, preferably from 20% to 100%, preferably from 30% to 100%, more preferably from 40% to 100%, even more preferably from 50% to 100%, yet more preferably from 60% to 100%, or most preferably from 70% to 100%, or even most preferably from 90% to 100% malted grain and/or malted barley. In a particular embodiment the grist comprises approximately 50% malted grain, e.g., malted barley, and approximately 50% adjunct, e.g., unmalted grain, such as unmalted barley.

Malted grain used in the process of the first aspect may comprise any malted grain, and preferably malted grain selected from malted barley, wheat, rye, sorghum, millet, corn, and rice, and most preferably malted barley.

The adjunct used in the process of the first aspect may be obtained from tubers, roots, stems, leaves, legumes, cereals and/or whole grain. The adjunct may comprise raw and/or refined starch and/or sugar containing material derived from plants like wheat, rye, oat, corn, rice, milo, millet, sorghum, potato, sweet potato, cassava, tapioca, sago, banana, sugar beet and/or sugar cane. Preferably, the adjunct comprises unmalted grain, e.g., unmalted grain selected from the list consisting of barley, wheat, rye, sorghum, millet, corn, and rice, and most preferably unmalted barley. Adjunct comprising readily fermentable carbohydrates such as sugars or syrups may be added to the barley malt mash before, during or after mashing process of the invention but is preferably added after the mashing process.

According to the invention, a pullulanase (E.C. 3.2.1.41) enzyme activity is exogenously supplied and present in the mash. The pullulanase may be added to the mash ingredients, e.g., the water and/or the grist before, during or after forming the mash. In a particularly preferred embodiment an alpha-amylase (E.C. 3.2.1.1) and/or a glucoamylase (E.C. 3.2.1.3), is added and present in the mash together with the pullulanase.

In another preferred embodiment, a further enzyme is added to the mash, said enzyme being selected from the group consisting of isoamylase, protease, laccase, xylanase, lipase, phospholipolase, phytase, phytin and esterase.

During the mashing process, starch extracted from the grist is gradually hydrolyzed into fermentable sugars and smaller dextrins. Preferably, the mash is starch negative to iodine testing, before extracting the wort.

The mashing process generally applies a controlled stepwise increase in temperature, where each step favors one enzymatic action over the other, eventually degrading proteins, cell walls and starch. Mashing temperature profiles are generally known in the art. In the present invention the saccharification (starch degradation) step in the mashing process is preferably performed between 60° C. and 66° C., more preferably between 61° C. and 65° C., even more preferably between 62° C. and 64° C., and most preferably between 63° C. and 64° C. In a particular embodiment of the present invention the saccharification temperature is 64° C.

Obtaining the wort from the mash typically includes straining the wort from the spent grains, i.e., the insoluble grain and husk material forming part of grist. Hot water may be run through the spent grains to rinse out, or sparge, any remaining extract from the grist. The application of a thermostable cellulase in the process of the present invention results in efficient reduction of beta-glucan level facilitating wort straining thus ensuring reduced cycle time and high extract recovery. Preferably the extract recovery is at least 80%, preferably at least 81%, more preferably at least 82%, even more preferably at least 83%, such as at least 84%, at least 85%, at least 86%, at least 87%, at least 88%, at least 89%, at least 90%, and most preferably at least 91%.

Following the separation of the wort from the spent grains of the grist of any of the aforementioned embodiments of the first aspect, the wort may be used as it is or it may be dewatered to provide a concentrated and/or dried wort. The concentrated and/or dried wort may be used as brewing extract, as malt extract flavoring, for non-alcoholic malt beverages, malt vinegar, breakfast cereals, for confectionary etc.

In a preferred embodiment, the wort is fermented to produce an alcoholic beverage, preferably a beer, e.g., ale, strong ale, bitter, stout, porter, lager, export beer, malt liquor, barley wine, happoushu, high-alcohol beer, low-alcohol beer, low-calorie beer or light beer. Fermentation of the wort may include pitching the wort with a yeast slurry comprising fresh yeast, i.e., yeast not previously used for the invention or the yeast may be recycled yeast. The yeast applied may be any yeast suitable for beer brewing, especially yeasts selected from *Saccharomyces* spp. such as *S. cerevisiae* and *S. uvarum*, including natural or artificially produced variants of these organisms. The methods for fermentation of wort for production of beer are well known to the person skilled in the arts.

The process of the invention may include adding silica hydrogel to the fermented wort to increase the colloidal stability of the beer. The processes may further include adding kieselguhr to the fermented wort and filtering to render the beer bright.

According to an aspect of the invention is provided beer produced from the wort of the second or third aspect, such as a beer produced by fermenting the wort to produce a beer. The beer may be any type of beer, e.g., ales, strong ales, stouts, porters, lagers, bitters, export beers, malt liquors, happoushu, high-alcohol beer, low-alcohol beer, low-calorie beer or light beer.

Enzymes

The enzymes to be applied in the present invention should be selected for their ability to retain sufficient activity at the process temperature of the processes of the invention, as well as under the pH regime in the mash and should be added in effective amounts. The enzymes may be derived from any source, preferably from a plant or an alga, and more preferably from a microorganism, such as from a bacterium or a fungus.

Pullulanase (E.C. 3.2.1.41)

A preferred pullulanase enzyme to be used in the processes and/or compositions of the invention is a pullulanase having an amino acid sequence which is at least 50%, such as at least 55%, such as at least 60%, such as at least 65%, such as at least 66%, such as at least 70%, such as at least 75%, such as at least 80%, such as at least 85%, such as at least 86%, such as at least 87%, such as at least 88%, such as at least 89%, such as at least 90%, such as at least 95%, such as at least 98% or even 100% identical to the sequence shown in SEQ ID NO: 4; ion particular when aligned using the Program Needle using Matrix: BLOSUM62; Gap initiation penalty: 10.0; Gap extension penalty: 0.5; Gapless Identity Matrix.

Most preferably the pullulanase is derived from *Bacillus acidopullulyticus*. The pullulanase may have the amino acid sequence disclosed by Kelly et al., 1994 (*FEMS Microbiol. Letters* 115: 97-106) (SEQ ID NO: 6) or a homologous sequence.

Isoamylase (E.C. 3.2.1.68)

Another enzyme applied in the processes and/or compositions of the invention may be an alternative debranching enzyme, such as an isoamylase (E.C. 3.2.1.68). Isoamylase hydrolyzes alpha-1,6-D-glucosidic branch linkages in amylopectin and beta-limit dextrins and can be distinguished from pullulanases by the inability of isoamylase to attack pullulan, and by the limited action on alpha-limit dextrins. Isoamylase may be added in effective amounts well known to the person skilled in the art. Isoamylase may be added alone or together with a pullulanase.

Alpha-Amylase (EC 3.2.1.1)

A particular alpha-amylase enzyme to be used in the processes and/or compositions of the invention may be a *Bacillus* alpha-amylase. Well-known *Bacillus* alpha-amylases include alpha-amylase derived from a strain of *B. licheniformis*, *B. amyloliquefaciens*, and *B. stearothermophilus*. In the context of the present invention, a contemplated *Bacillus* alpha-amylase is an alpha-amylase as defined in WO 99/19467 on page 3, line 18 to page 6, line 27. A preferred alpha-amylase has an amino acid sequence having at least 90% identity to SEQ ID NO: 4 in WO 99/19467 (herein disclosed as SEQ ID NO: 7), such as at least 92%, at least 95%, at least 96%, at least 97%, at least 98%, or particularly at least 99%. Most preferred maltogenic alpha-amylase is SEQ ID NO: 9 or comprise the variants thereof disclosed in WO 99/43794. Contemplated variants and hybrids are described in WO 96/23874, WO 97/41213, and WO 99/19467. Specifically contemplated is an alpha-amylase (E.C. 3.2.1.1) from *B. stearothermophilus* having the amino acid sequence disclosed as SEQ ID NO: 3 in WO 99/19467 (herein disclosed as SEQ ID NO: 10) with the mutations: I181*+G182*+N193F.

*Bacillus* alpha-amylases may be added in the amounts of 1.0-1000 NU/kg DS, preferably from 2.0-500 NU/kg DS, preferably 10-200 NU/kg DS.

Another particular alpha-amylase to be used in the processes of the invention may be any fungal alpha-amylase, e.g., an alpha-amylase derived from a species within *Aspergillus*, and preferably from a strain of *Aspergillus niger*. Especially contemplated are fungal alpha-amylases which exhibit a high identity, i.e., at least 50%, at least 55%, at least 60%, at least 65%, at least 70%, at least 75%, at least 80%, at least 85% or even at least 90% identity to the amino acid sequences shown SEQ ID NO: 1 in WO 2002/038787 (herein disclosed as SEQ ID NO: 11). Fungal alpha-amylases may be added in an amount of 1-1000 AFAU/kg DS, preferably from 2-500 AFAU/kg DS, preferably 20-100 AFAU/kg DS.

Glucoamylases (E.C.3.2.1.3)

A further particular enzyme to be used in the processes and/or compositions of the invention may be a glucoamylase (E.C.3.2.1.3) derived from a microorganism or a plant. Preferred are glucoamylases of fungal or bacterial origin selected from the group consisting of *Aspergillus* glucoamylases, in particular *A. niger* G1 or G2 glucoamylase (Boel et al., 1984, EMBO J. 3(5): 1097-1102), or variants thereof, such as disclosed in WO 92/00381 and WO 00/04136; the *A. awamori* glucoamylase (WO 84/02921), *A. oryzae* (*Agric. Biol. Chem.*, 1991, 55(4): 941-949), or variants or fragments thereof.

Other contemplated glucoamylases include *Talaromyces* glucoamylases, in particular derived from *Talaromyces emersonii* (WO 99/28448), *Talaromyces leycettanus* (U.S. Pat. No. Re. 32,153), *Talaromyces duponti*, and *Talaromyces thermophilus* (U.S. Pat. No. 4,587,215). Preferred glucoamylases include the glucoamylases derived from *Aspergillus oryzae*, such as a glucoamylase having at least 90%, at least 92%, at least 95%, at least 96%, at least 97%, at least 98%, or particularly at least 99% or even at least 90% identity to the amino acid sequence shown in SEQ ID NO:2 in WO00/04136. Other preferred glucoamylases include the glucoamylases derived from *Talaromyces emersonii* such as a glucoamylase having at least 90%, at least 92%, at least 95%, at least 96%, at least 97%, at least 98%, or particularly at least 99% or even at least 90% identity to the amino acid sequence of *Talaromyces emersonii* (WO 99/28448).

Bacterial glucoamylases contemplated include glucoamylases from the genus *Clostridium*, in particular *C. thermoamylolyticum* (EP 135,138), and *C. thermohydrosulfuricum* (WO 86/01831).

Also contemplated are the commercial products AMG 200L; AMG 300 L; SAN™ SUPER and AMG™ E (from Novozymes); OPTIDEX™ 300 (from Genencor Int.); AMIGASE™ and AMIGASE™ PLUS (from DSM); G-ZYME™ G900 (from Enzyme Bio-Systems); G-ZYME™ G990 ZR (*A. niger* glucoamylase and low protease content). Glucoamylases may be added in effective amounts well known to the person skilled in the art.

Protease

Suitable proteases include microbial proteases, such as fungal and bacterial proteases. Preferred proteases are acidic proteases, i.e., proteases characterized by the ability to hydrolyze proteins under acidic conditions below pH 7.

The proteases are responsible for reducing the overall length of high-molecular-weight proteins to low-molecular-weight proteins in the mash. The low-molecular-weight proteins are a necessity for yeast nutrition and the high-molecular-weight-proteins ensure foam stability. Thus it is well-known to the skilled person that protease should be added in a balanced amount which at the same time allows amble free amino acids for the yeast and leaves enough high-molecular-weight-proteins to stabilize the foam. Proteases may be added in the amounts of 0.1-1000 AU/kg DS, preferably 1-100 AU/kg DS and most preferably 5-25 AU/kg DS.

Cellulase (E.C. 3.2.1.4)

The cellulase may be of microbial origin, such as derivable from a strain of a filamentous fungus (e.g., *Aspergillus, Trichoderma, Humicola, Fusarium*). Specific examples of cellulases include the endoglucanase (endoglucanase I) obtainable from *H. insolens* and further defined by the amino acid sequence of FIG. 14 in WO 91/17244 (herein disclosed as SEQ ID NO: 12) and the 43 kD *H. insolens* endoglucanase described in WO 91/17243.

A particular cellulase to be used in the processes of the invention may be an endo-glucanase, such as an endo-1,4-beta-glucanase. Especially contemplated is the beta-glucanase shown in SEQ. ID. NO: 2 in WO 2003/062409 (herein disclosed as SEQ ID NO: 14) and homologous sequences. Commercially available cellulase preparations which may be used include CELLUCLAST®, CELLUZYME®, CEREFLO® and ULTRAFLO® (available from Novozymes A/S), LAMINEX™ and SPEZYME® CP (available from Genencor Int.) and ROHAMENT® 7069 W (available from Röhm, Germany).

Beta-glucanases may be added in the amounts of 1.0-10000 BGU/kg DS, preferably from 10-5000 BGU/kg DS, preferably from 50-1000 BGU/kg DS and most preferably from 100-500 BGU/kg DS.

Materials and Methods

Enzymes

Pullulanase 1 derived from *Bacillus acidopullulyticus* and having the sequence showed in SEQ ID NO: 1. Pullulanase 1 is available from Novozymes as Promozyme 400L.

Pullulanase 2 derived from *Bacillus deramificans* (U.S. Pat. No. 5,736,375) and having the sequence showed in SEQ ID NO: 2. Pullulanase 2 is available from Novozymes as Promozyme D2.

Pullulanase 3 derived from *Bacillus acidopullulyticus* and having the sequence showed in SEQ ID NO: 4.

Acid fungal alpha-amylase derived from *Aspergillus niger* and having the sequence showed in SEQ ID NO: 11.

Glucoamylase G1 derived from *Aspergillus niger* (Boel et al., supra).

Methods

Alpha-Amylase Activity (NU)

Alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) equals 1000 NU. One KNU is defined as the amount of enzyme which, under standard conditions (i.e., at 37° C.+/−0.05; 0.0003 M $Ca^{2+}$; and pH 5.6) degrades 5.26 g starch dry matter (Merck Amylum solubile).

Acid Alpha-Amylase Activity (AFAU)

Acid alpha-amylase activity may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

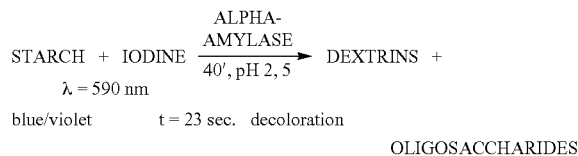

Standard Conditions/Reaction Conditions:
Substrate: Soluble starch, approx. 0.17 g/L
Buffer: Citrate, approx. 0.03 M
Iodine (I2): 0.03 g/L
CaCl2: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL
Glucoamylase Activity (AGU)

The Novo Glucoamylase Unit (AGU) is defined as the amount of enzyme, which hydrolyzes 1 micromole maltose per minute at 37° C. and pH 4.3.

The activity is determined as AGU/ml by a method modified after (AEL-SM-0131, available on request from Novozymes) using the Glucose GOD-Perid kit from Boehringer Mannheim, 124036. Standard: AMG-standard, batch 7-1195, 195 AGU/ml. 375 microL substrate (1% maltose in 50 mM Sodium acetate, pH 4.3) is incubated 5 minutes at 37° C. 25 microL enzyme diluted in sodium acetate is added. The reaction is stopped after 10 minutes by adding 100 microL 0.25 M NaOH. 20 microL is transferred to a 96 well microtitre plate and 200 microL GOD-Perid solution (124036, Boehringer Mannheim) is added. After 30 minutes at room temperature, the absorbance is measured at 650 nm and the activity calculated in AGU/ml from the AMG-standard. A detailed description of the analytical method (AEL-SM-0131) is available on request from Novozymes.

Pullulanase Activity (PUN):

One pullulanase unit (PUN) is defined as the amount of enzyme, which is capable of forming 1 micromole glucose from pullulan substrate per minute at 50° C. in a pH 5 citrate buffer.

Pullulanase samples are incubated with substrate (red pullulan). Endo-pullulanase hydrolyses the alpha-1,6-glycosidic bonds in red pullulan, releasing red substrate degradation products. Non-degraded substrate is precipitated using ethanol. The amount of color released is measured spectrophotometrically at 510 nm and is proportional to the endo-pullulanase activity in the sample. The color formation of samples is compared to the color formation produced by samples with known pullulanase activity.

Pullulanase is a pullulan 6-glucano-hydrolase with the enzyme classification number E.C.3.2.1.41.
Reaction Conditions

| | |
|---|---|
| Temperature | 50° C. ± 2° C. |
| pH | 5.0 |
| Substrate concentration | 0.67% red pullulan |
| Enzyme concentration | 0.04-0.13 PUN/ml |
| Reaction time | 30 min. |
| Wavelength | 510 nm |

Reagents/Substrates
Potassium chloride solution 0.5 M
Red pullulan substrate 2%. Supplier Megazyme, Australia
Citrate buffer 0.05 M pH 5.0
Citrate buffer 0.05 M pH 5.0 with 25 mM cysteine
Ethanol 99.8%
Pullulanase Standard preparation of 904 PUN/g diluted into citrate buffer 0.05 M to a standard dilution series from 0.05-0.20 PUN/ml
Blank Citrate buffer 0.05 M
Enzyme samples are diluted in citrate buffer 0.05 M to an activity between 0.06-0.20 PUN/ml and compared to the standard dilution series.

Example 1

In this example, the ability of different pullulanases to reduce the amount of non-fermentable carbohydrates (dextrin/DP4/4+) in a wort was analyzed.

100% well modified malt was mashed using a mashing temperature profile comprising 46° C. for 26 minutes, followed by a 1° C./minute increase till 64° C. after which the temperature was held constant. Samples were collected at 98, 128 and 158 minutes.

Enzymes were added at 0 minutes. Glucoamylase and alpha-amylase were added to all treatments in amounts of 1000 AGU/kg DS and 250 AFAU/kg DS respectively. Pullulanase was added according to table 1.

The samples were boiled 10 minutes and filtered (Pore size 0.20 micro-m). The samples were analyzed by HPLC and % non fermentable carbohydrate (DP4/4+) was calculated.

TABLE 1

% non fermentable carbohydrate after mashing times of 98, 128 and 158 minutes.

| Type of pullulanase | Amount in mg/kg DS | Mashing time | | |
|---|---|---|---|---|
| | | 98 minutes | 128 minutes | 158 minutes |
| None | 0 | 28.87 | 25.16 | 22.94 |
| Pullulanase 1 | 0.74 | 27.64 | 24.55 | 21.96 |
| Pullulanase 1 | 3.65 | 23.96 | 21.35 | 18.92 |
| Pullulanase 1 | 7.25 | 20.71 | 17.74 | 16.11 |
| Pullulanase 1 | 14.39 | 16.36 | 14.47 | 13.22 |
| Pullulanase 2 | 1.86 | 28.34 | 25.21 | 22.79 |
| Pullulanase 2 | 9.26 | 26.81 | 23.28 | 21.36 |
| Pullulanase 2 | 18.40 | 25.68 | 22.33 | 20.17 |
| Pullulanase 2 | 36.59 | 23.56 | 20.58 | 18.35 |
| Pullulanase 3 | 1.37 | 27.11 | 23.38 | 20.51 |
| Pullulanase 3 | 2.74 | 24.46 | 20.93 | 18.18 |

The data in table 1 was used to calculate, by regression, the enzyme dosages of pullulanase 1 and pullulanase 2 needed to get the same effect as 2.74 mg enzyme protein/kg of pullulanase 3 (see table 2).

TABLE 2

Pullulanase enzyme protein mg/kg DS needed to achieve the same effect as with 2.74 mg Pullulanase 3 and mashing times of 98, 128 and 158 minutes.

| Mashing time | Pullulanase 1 | Pullulanase 2 |
|---|---|---|
| 98 minutes | 3.38 | 27.33 |
| 128 minutes | 4.04 | 31.06 |
| 158 minutes | 4.56 | 40.37 |

From these results it can be seen that Pullulanase 3 is the most efficient enzyme. Consequently, less Pullulanase 3 enzyme protein is needed to reduce the amount of non-fermentable carbohydrates (dextrin/DP4/4+) and thereby increase attenuation of the wort.

Example 2

The pH profile and temperature profile of different pullulanases were analyzed in the present example.

The pH and temperature profile investigations were based on relative enzyme activity analysis with the conditions described below.

Principals of the Analytical Method:

The alpha-1,6-glycosidic bonds in pullulan were hydrolyzed by a pullulanase enzyme and the increased reducing sugar capacity was detected by a modified Somogyi-Nelson method.

In the present experiment the activity is assessed as relative activity, where the most active sample is given as 100%. The assay conditions are as follows:

Buffer: citrate 0.1 M+0.2 M phosphate (adjusted in the pH profile, pH 5 in temperature profile)
Substrate: 0.2% pullulan Sigma (p-4516)
Temperature: 60° C. in pH profile, adjusted in temperature profile
Reaction time: 30 minutes The reducing sugars released by pullulanases were detected according to the principle described in Nelson, 1944, *J. Biol. Chem.* 153: 375-380 and Somogyi, 1945, *J. Biol. Chem.* 160: 61-68. In brief, the hydrolysis reaction is stopped by adding Somogyi's cobber reagent in a volume corresponding to the sample volume (e.g., 2 ml to a sample of 2 ml). The samples are boiled for 20 minutes and cooled down prior to the color reaction. This reaction is performed by adding Nelson's reagent corresponding to ½ the volume of the sample (e.g., 2 ml to 4 ml sample+Somogyi's cobber reagent). The samples are mixed for 2 minutes followed by addition of water in the same amount as Nelson's reagent. The samples are incubated 30 minutes in the dark and measured in a spectrophotometer at 540 nm.

Reagents can be prepared as follows:

Somogyi's Cobber Reagent:

Dissolve 70.2 g $Na_2HPO_4 \times 2H_2O$ and 80.0 g $KNAC_4H_4O_6 \times 4H_2O$ (kaliumsodiumtartrat) in 1000 ml $H_2O$ (heat slightly). Furthermore add 60 g NaOH; 16.0 g $CuSO_4 \times 5H_2O$ and 360.0 g $Na_2SO_4$ and fill to 2000 ml. Adjust pH to 10.8 with NaOH Nelson's Reagent:

Dissolve 100.0 g $(NH_4)_6Mo_7O_{24} \times 7H_2O$ in 1200 ml $H_2O$. Add 84.0 ml $H_2SO_4$ carefully. Additionally, dissolve 12.00 g $Na_2HAsO_4 \times 7H_2O$ (disodiumhydrogenarsenate) in 100 ml $H_2O$, and add this solution slowly to the first solution and fill to 2000 ml.

The pH and temperature profiles for the three pullulanases are given in table 3 and 4 below.

TABLE 3 pH profile given in relative (%) enzyme activity at 60° C.

| pH | Pullulanase 1 | Pullulanase 2 | Pullulanase 3 |
|---|---|---|---|
| 2.4 | 2.2 | 1 | 0.2 |
| 2.8 | 6 | 2.4 | 30.7 |
| 3.7 | 10.8 | 68.5 | 90 |
| 4.2 | 23.1 | 100 | 100 |
| 5 | 94 | 77.4 | 92.4 |
| 5.8 | 92.8 | 31.7 | 74.2 |
| 6.3 | 43.1 | 4.4 | 45.3 |

TABLE 3-continued pH profile given in relative (%) enzyme activity at 60° C.

| pH | Pullulanase 1 | Pullulanase 2 | Pullulanase 3 |
|---|---|---|---|
| 6.7 | 3.7 | 0 | 1.8 |
| 7.3 | 0 | 0 | 0 |

TABLE 4

Temperature profile given in relative (%) enzyme activity at pH 5.0

| Temp. ° C. | Pullulanase 1 | Pullulanase 2 | Pullulanase 3 |
|---|---|---|---|
| 30 | 22.8 | 36.7 | 19.7 |
| 45 | 64.4 | 72.5 | 47.3 |
| 55 | 100 | 100 | 76.8 |
| 60 | 99.6 | 85.2 | 92.6 |
| 62.5 | 87.1 | 70 | 101.2 |
| 65 | 42.1 | 54.4 | 100 |
| 70 | 9.4 | 12.7 | 75.6 |

These results show that pullulanase 3 has a broad pH profile and activity at high temperatures when compared to the other two pullulanases. These properties make pullulanase 3 a very robust enzyme in brewing (mashing conditions), in particular for saccharification temperatures between 62° C. and 65° C.

Example 3

Infusion mashing test were made with Pullulanase 1 and 3 (SEQ ID NOS: 1 and 4). 6 mashing samples were prepared with 100% barley as substrate (grist).

Barley (DS %: 86.73) was milled and for each sample 50.0 g (total DS 43.34 g) were mixed with 200 g tap water at 50° C. and 3.0 ml 1 M $H_3PO_4$.

All samples were added an identical enzyme mix with no pullulanase.

Samples 1-6 were then added pullulanase according to the following table:

Enzyme Dose Activity/g

| Sample no. | Pullulanase 1 PUN/g | Pullulanase 3 PUN/g |
|---|---|---|
| 1 | 0.1 | — |
| 2 | 0.2 | — |
| 3 | 0.5 | — |
| 4 | — | 0.1 |
| 5 | — | 0.2 |
| 6 | — | 0.5 |

The samples were then tested in automated mashing equipment running the following program.

| Time in minutes | Temp. ° C. |
|---|---|
| 0-30 | 50 |
| 30-44 | rising to 64 |
| 44-104 | 64 |
| 104-120 | rising to 80 |
| 120-140 | 80 |
| 140-155 | falling to 20 |

After mashing all samples were added tap water to a total of 300 g and filtered. The filtered samples were then boiled for 10 minutes and diluted 1:1 with deionised water. Subsamples of 50 ml were centrifuged and subjected to standard density analysis for calculation of RDF % (real degree of fermentation). The results are given as RDF % and wort sugar (DP2 and DP4+) in %.

| PUN/g | Pullulanase 1 | Pullulanase 3 |
|---|---|---|
| 0 | 0 | 0 |
| 0.1 | 64 | 64.6 |
| 0.2 | 65 | 66.1 |
| 0.5 | 67.3 | 69.5 |

|  | Pullulanase 1 | | Pullulanase 3 | |
|---|---|---|---|---|
| PUN/g | DP2 | DP4+ | DP2 | DP4+ |
| 0 | 48.5 | 31.5 | 48.5 | 31.5 |
| 0.1 | 48.5 | 30 | 49 | 29 |
| 0.2 | 49.5 | 29 | 50 | 27.5 |
| 0.5 | 50.5 | 36.5 | n.d. | n.d. |

The results show that pullulanase 3 is clearly better than pullulanase 1 for making a high % RDF, and still pullulanase 3 is capable of producing maltose levels (DP2 levels) even better than pullulanase 1.

Example 4

Infusion mashing test were made with Pullulanase 3 (SEQ ID NO: 4) to evaluate the maltose generating properties of pullulanase 3. 6 mashing samples were prepared with 100% barley as substrate (grist).
Barley (DS %: 86.73) was milled and for each sample 50.0 g (total DS 43.34 g) were mixed with 200 g tap water at 50° C. and 5% $Na_2SO_3$ and 1 M $H_3PO_4$
All samples were added an identical enzyme mix with no pullulanase.
Samples 1-6 were then added pullulanase 3 according to the following table:

| Sample no. | Pullulanse 3 PUN/g |
|---|---|
| 1 | — |
| 2 | 0.1 |
| 3 | 0.3 |
| 4 | 0.5 |
| 5 | 1.0 |
| 6 | 2.0 |

The samples were then tested in automated mashing equipment running the following program.

| Time in minutes | Temp. ° C. |
|---|---|
| 0-30 | 50 |
| 30-44 | rising to 64 |
| 44-104 | 64 |
| 104-120 | rising to 80 |
| 120-140 | 80 |
| 140-155 | falling to 20 |

After mashing all samples were added tap water to a total of 300 g and filtered. The filtered samples were then boiled for 10 minutes and diluted 1:1 with deionized water. Subsamples of 50 ml were centrifuged and subjected to analysis. The results were as follows:

| PUN/g | % glucose | % maltose | % dextrin | RDF % |
|---|---|---|---|---|
| 0 | 3.8 | 47.5 | 34 | 61.2 |
| 0.1 | 3.8 | 48.2 | 32 | 63.2 |
| 0.3 | 3.8 | 49.8 | 28.8 | 65.7 |
| 0.5 | 3.7 | 51.2 | 26.4 | 68.6 |
| 1 | 3.7 | 52.6 | 23.9 | 71 |
| 2 | 3.6 | 55.6 | 20.1 | 74.3 |

The results show that maltose concentration is increasing with increasing dosage of pullulanase 3, and the increase in maltose % is followed by the increase in attenuation (RDF %). The dextrin fraction (HPLC analysis DP4/4+) is at the same time decreasing.

Only barley beta-amylase can produce maltose in this reaction, and pullulanase 3 is facilitating the action of barley beta-amylase.

Glucose concentration is low and not effected by the action of pullulanase 3 which is an advantage when fermenting the produced wort. Pullulanase 3 help degrading dextrin and facilitate formation of maltose, by the barley beta-amylase, and by this increase attenuation (RDF %) of the wort.

The invention claimed is:

1. A process for producing a brewers wort comprising forming a mash from a grist, and contacting said mash with a pullulanase, a glucoamylase, and an alpha-amylase, wherein said pullulanase has an amino acid sequence which is at least 98% identical to the amino acid sequence shown in SEQ ID NO: 4.

2. The process according to claim 1, wherein the pullulanase is derived from *Bacillus acidopullulyticus*.

3. The process according to claim 1, wherein the glucoamylase and/or alpha-amylase is derived from *Aspergillus niger* or *Talaromyces emersonii*.

4. The process according to claim 1, further comprising contacting the mash with an enzyme selected from the group consisting of cellulase, isoamylase, xylanase and protease.

5. The process according to claim 1, wherein the grist comprises malted and/or unmalted grain.

6. The process according to claim 1, wherein the unmalted grain and/or the malted grain is selected from the list consisting of barley, wheat, rye, sorghum, millet, corn and rice.

7. The process according to claim 1, wherein the malted grain comprises malted grain selected from malted barley, wheat, rye, sorghum, millet, corn, and rice.

8. The process according to claim 1, wherein the wort is concentrated and/or dried.

9. The process according to claim 1, further comprising fermenting the wort to obtain an alcoholic beverage.

10. The process according to claim 9, wherein the alcoholic beverage is a beer.

11. The process according to claim 10, wherein the beer is ale, strong ale, bitter, stout, porter, lager, export beer, malt liquor, barley wine, happoushu, high-alcohol beer, low-alcohol beer, low-calorie beer or light beer.

12. The process of claim 1, wherein said pullulanase has an amino acid sequence which is 100% identical to the amino acid sequence shown in SEQ ID NO: 4.

* * * * *

SEQUENCE LISTING

```
<160> NUMBER OF SEQ ID NOS: 14

<210> SEQ ID NO 1
<211> LENGTH: 921
<212> TYPE: PRT
<213> ORGANISM: Bacillus acidopullulyticus
<220> FEATURE:
<221> NAME/KEY: mat_peptide
<222> LOCATION: (1)..(921)

<400> SEQUENCE: 1

Asp Ser Thr Ser Thr Lys Val Ile Val His Tyr His Arg Phe Asp Ser
1               5                   10                  15

Asn Tyr Thr Asn Trp Asp Val Trp Met Trp Pro Tyr Gln Pro Val Asn
```

```
                20                  25                  30
Gly Asn Gly Ala Ala Tyr Gln Phe Thr Gly Thr Asn Asp Asp Phe Gly
            35                  40                  45
Ala Val Ala Asp Thr Gln Val Pro Gly Asp Asn Thr Gln Val Gly Leu
 50                  55                  60
Ile Val Arg Lys Asn Asp Trp Ser Glu Lys Asn Thr Pro Asn Asp Leu
 65                  70                  75                  80
His Ile Asp Leu Ala Lys Gly His Glu Val Trp Ile Val Gln Gly Asp
                85                  90                  95
Pro Thr Ile Tyr Tyr Asn Leu Ser Asp Ala Gln Ala Ala Ile Pro
                100                 105                 110
Ser Val Ser Asn Ala Tyr Leu Asp Asp Glu Lys Thr Val Leu Ala Lys
            115                 120                 125
Leu Ser Met Pro Met Thr Leu Ala Asp Ala Ser Gly Phe Thr Val
            130                 135                 140
Ile Asp Lys Thr Thr Gly Glu Lys Ile Pro Val Thr Ser Ala Val Ser
145                 150                 155                 160
Ala Asn Pro Val Thr Ala Val Leu Val Gly Asp Leu Gln Gln Ala Leu
            165                 170                 175
Gly Ala Ala Asn Asn Trp Ser Pro Asp Asp His Thr Leu Leu Lys
            180                 185                 190
Lys Ile Asn Pro Asn Leu Tyr Gln Leu Ser Gly Thr Leu Pro Ala Gly
            195                 200                 205
Thr Tyr Gln Tyr Lys Ile Ala Leu Asp His Ser Trp Asn Thr Ser Tyr
            210                 215                 220
Pro Gly Asn Asn Val Ser Leu Thr Val Pro Gln Gly Gly Glu Lys Val
225                 230                 235                 240
Thr Phe Thr Tyr Ile Pro Ser Thr Asn Gln Val Phe Asp Ser Val Asn
                245                 250                 255
His Pro Asn Gln Ala Phe Pro Thr Ser Ser Ala Gly Val Gln Thr Asn
            260                 265                 270
Leu Val Gln Leu Thr Leu Ala Ser Ala Pro Asp Val Thr His Asn Leu
            275                 280                 285
Asp Val Ala Ala Asp Gly Tyr Lys Ala His Asn Ile Leu Pro Arg Asn
            290                 295                 300
Val Leu Asn Leu Pro Arg Tyr Asp Tyr Ser Gly Asn Asp Leu Gly Asn
305                 310                 315                 320
Val Tyr Ser Lys Asp Ala Thr Ser Phe Arg Val Trp Ala Pro Thr Ala
                325                 330                 335
Ser Asn Val Gln Leu Leu Leu Tyr Asn Ser Glu Lys Gly Ser Ile Thr
            340                 345                 350
Lys Gln Leu Glu Met Gln Lys Ser Asp Asn Gly Thr Trp Lys Leu Gln
            355                 360                 365
Val Ser Gly Asn Leu Glu Asn Trp Tyr Tyr Leu Tyr Gln Val Thr Val
            370                 375                 380
Asn Gly Thr Thr Gln Thr Ala Val Asp Pro Tyr Ala Arg Ala Ile Ser
385                 390                 395                 400
Val Asn Ala Thr Arg Gly Met Ile Val Asp Leu Lys Ala Thr Asp Pro
                405                 410                 415
Ala Gly Trp Gln Gly Asp His Glu Gln Thr Pro Ala Asn Pro Val Asp
            420                 425                 430
Glu Val Ile Tyr Glu Ala His Val Arg Asp Phe Ser Ile Asp Ala Asn
            435                 440                 445
```

```
Ser Gly Met Lys Asn Lys Gly Lys Tyr Leu Ala Phe Thr Glu His Gly
    450                 455                 460

Thr Lys Gly Pro Asp His Val Lys Thr Gly Ile Asp Ser Leu Lys Glu
465                 470                 475                 480

Leu Gly Ile Thr Thr Val Gln Leu Gln Pro Val Glu Glu Phe Asn Ser
                    485                 490                 495

Ile Asp Glu Thr Gln Pro Asp Thr Tyr Asn Trp Gly Tyr Asp Pro Arg
                500                 505                 510

Asn Tyr Asn Val Pro Glu Gly Ala Tyr Ala Thr Thr Pro Glu Gly Thr
            515                 520                 525

Ala Arg Ile Thr Glu Leu Lys Gln Leu Ile Gln Ser Leu His Gln Gln
    530                 535                 540

Arg Ile Gly Val Asn Met Asp Val Val Tyr Asn His Thr Phe Asp Val
545                 550                 555                 560

Met Val Ser Asp Phe Asp Lys Ile Val Pro Gln Tyr Tyr Arg Thr
                    565                 570                 575

Asp Ser Asn Gly Asn Tyr Thr Asn Gly Ser Gly Cys Gly Asn Glu Phe
                580                 585                 590

Ala Thr Glu His Pro Met Ala Gln Lys Phe Val Leu Asp Ser Val Asn
            595                 600                 605

Tyr Trp Val Asn Glu Tyr His Val Asp Gly Phe Arg Phe Asp Leu Met
    610                 615                 620

Ala Leu Leu Gly Lys Asp Thr Met Ala Lys Ile Ser Asn Glu Leu His
625                 630                 635                 640

Ala Ile Asn Pro Gly Ile Val Leu Tyr Gly Glu Pro Trp Thr Gly Gly
                    645                 650                 655

Thr Ser Gly Leu Ser Ser Asp Gln Leu Val Thr Lys Gly Gln Gln Lys
                660                 665                 670

Gly Leu Gly Ile Gly Val Phe Asn Asp Asn Ile Arg Asn Gly Leu Asp
            675                 680                 685

Gly Asn Val Phe Asp Lys Thr Ala Gln Gly Phe Ala Thr Gly Asp Pro
    690                 695                 700

Asn Gln Val Asp Val Ile Lys Asn Gly Val Ile Gly Ser Ile Gln Asp
705                 710                 715                 720

Phe Thr Ser Ala Pro Ser Glu Thr Ile Asn Tyr Val Thr Ser His Asp
                    725                 730                 735

Asn Met Thr Leu Trp Asp Lys Ile Leu Ala Ser Asn Pro Ser Asp Thr
                740                 745                 750

Glu Ala Asp Arg Ile Lys Met Asp Glu Leu Ala His Ala Val Val Phe
            755                 760                 765

Thr Ser Gln Gly Val Pro Phe Met Gln Gly Gly Glu Glu Met Leu Arg
    770                 775                 780

Thr Lys Gly Gly Asn Asp Asn Ser Tyr Asn Ala Gly Asp Ser Val Asn
785                 790                 795                 800

Gln Phe Asp Trp Ser Arg Lys Ala Gln Phe Lys Asp Val Phe Asp Tyr
                    805                 810                 815

Phe Ser Ser Met Ile His Leu Arg Asn Gln His Pro Ala Phe Arg Met
                820                 825                 830

Thr Thr Ala Asp Gln Ile Lys Gln Asn Leu Thr Phe Leu Glu Ser Pro
            835                 840                 845

Thr Asn Thr Val Ala Phe Glu Leu Lys Asn Tyr Ala Asn His Asp Thr
    850                 855                 860
```

-continued

Trp Lys Asn Ile Ile Val Met Tyr Asn Pro Asn Lys Thr Ser Gln Thr
865                 870                 875                 880

Leu Asn Leu Pro Ser Gly Asp Trp Thr Ile Val Gly Leu Gly Asp Gln
            885                 890                 895

Ile Gly Glu Lys Ser Leu Gly His Val Met Gly Asn Val Gln Val Pro
        900                 905                 910

Ala Ile Ser Thr Leu Ile Leu Lys Gln
        915                 920

<210> SEQ ID NO 2
<211> LENGTH: 928
<212> TYPE: PRT
<213> ORGANISM: Bacillus deramificans
<220> FEATURE:
<221> NAME/KEY: mat_peptide
<222> LOCATION: (1)..(928)

<400> SEQUENCE: 2

Asp Gly Asn Thr Thr Ile Ile Val His Tyr Phe Arg Pro Ala Gly
1               5                   10                  15

Asp Tyr Gln Pro Trp Ser Leu Trp Met Trp Pro Lys Asp Gly Gly
            20                  25                  30

Ala Glu Tyr Asp Phe Asn Gln Pro Ala Asp Ser Phe Gly Ala Val Ala
        35                  40                  45

Ser Ala Asp Ile Pro Gly Asn Pro Ser Gln Val Gly Ile Ile Val Arg
50                  55                  60

Thr Gln Asp Trp Thr Lys Asp Val Ser Ala Asp Arg Tyr Ile Asp Leu
65                  70                  75                  80

Ser Lys Gly Asn Glu Val Trp Leu Val Glu Gly Asn Ser Gln Ile Phe
                85                  90                  95

Tyr Asn Glu Lys Asp Ala Glu Asp Ala Ala Lys Pro Ala Val Ser Asn
            100                 105                 110

Ala Tyr Leu Asp Ala Ser Asn Gln Val Leu Val Lys Leu Ser Gln Pro
        115                 120                 125

Leu Thr Leu Gly Glu Gly Ala Ser Gly Phe Thr Val His Asp Asp Thr
130                 135                 140

Ala Asn Lys Asp Ile Pro Val Thr Ser Val Lys Asp Ala Ser Leu Gly
145                 150                 155                 160

Gln Asp Val Thr Ala Val Leu Ala Gly Thr Phe Gln His Ile Phe Gly
                165                 170                 175

Gly Ser Asp Trp Ala Pro Asp Asn His Ser Thr Leu Leu Lys Lys Val
            180                 185                 190

Thr Asn Asn Leu Tyr Gln Phe Ser Gly Asp Leu Pro Glu Gly Asn Tyr
        195                 200                 205

Gln Tyr Lys Val Ala Leu Asn Asp Ser Trp Asn Pro Ser Tyr Pro
210                 215                 220

Ser Asp Asn Ile Asn Leu Thr Val Pro Ala Gly Gly Ala His Val Thr
225                 230                 235                 240

Phe Ser Tyr Ile Pro Ser Thr His Ala Val Tyr Asp Thr Ile Asn Asn
                245                 250                 255

Pro Asn Ala Asp Leu Gln Val Glu Ser Gly Val Lys Thr Asp Leu Val
            260                 265                 270

Thr Val Thr Leu Gly Glu Asp Pro Asp Val Ser His Thr Leu Ser Ile
        275                 280                 285

Gln Thr Asp Gly Tyr Gln Ala Lys Gln Val Ile Pro Arg Asn Val Leu
290                 295                 300

-continued

```
Asn Ser Ser Gln Tyr Tyr Tyr Ser Gly Asp Asp Leu Gly Asn Thr Tyr
305                 310                 315                 320

Thr Gln Lys Ala Thr Thr Phe Lys Val Trp Ala Pro Thr Ser Thr Gln
            325                 330                 335

Val Asn Val Leu Leu Tyr Asp Ser Ala Thr Gly Ser Val Thr Lys Ile
            340                 345                 350

Val Pro Met Thr Ala Ser Gly His Gly Val Trp Glu Ala Thr Val Asn
            355                 360                 365

Gln Asn Leu Glu Asn Trp Tyr Tyr Met Tyr Glu Val Thr Gly Gln Gly
            370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
                420                 425                 430

Ile Tyr Glu Met Asp Val Arg Asp Phe Ser Ile Asp Pro Asn Ser Gly
                435                 440                 445

Met Lys Asn Lys Gly Lys Tyr Leu Ala Leu Thr Glu Lys Gly Thr Lys
            450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Ser Asn Ser Val Asp
                485                 490                 495

Glu Thr Asp Pro Thr Gln Asp Asn Trp Gly Tyr Asp Pro Arg Asn Tyr
                500                 505                 510

Asp Val Pro Glu Gly Gln Tyr Ala Thr Asn Ala Asn Gly Asn Ala Arg
                515                 520                 525

Ile Lys Glu Phe Lys Glu Met Val Leu Ser Leu His Arg Glu His Ile
            530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

Ala Gly Asn Tyr Thr Asn Gly Ser Gly Thr Gly Asn Glu Ile Ala Ala
                580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
            610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Asp Asp Gln Leu Leu Thr Lys Gly Ala Gln Lys Gly Met
                660                 665                 670

Gly Val Ala Val Phe Asn Asp Asn Leu Arg Asn Ala Leu Asp Gly Asn
                675                 680                 685

Val Phe Asp Ser Ser Ala Gln Gly Phe Ala Thr Gly Ala Thr Gly Leu
                690                 695                 700

Thr Asp Ala Ile Lys Asn Gly Val Glu Gly Ser Ile Asn Asp Phe Thr
705                 710                 715                 720
```

-continued

```
Ser Ser Pro Gly Glu Thr Ile Asn Tyr Val Thr Ser His Asp Asn Tyr
            725                 730                 735

Thr Leu Trp Asp Lys Ile Ala Leu Ser Asn Pro Asn Asp Ser Glu Ala
        740                 745                 750

Asp Arg Ile Lys Met Asp Glu Leu Ala Gln Ala Val Val Met Thr Ser
    755                 760                 765

Gln Gly Val Pro Phe Met Gln Gly Gly Glu Met Leu Arg Thr Lys
770                 775                 780

Gly Gly Asn Asp Asn Ser Tyr Asn Ala Gly Ala Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
        820                 825                 830

Ala Asn Glu Ile Asn Ser His Leu Gln Phe Leu Asn Ser Pro Glu Asn
    835                 840                 845

Thr Val Ala Tyr Glu Leu Thr Asp His Val Asn Lys Asp Lys Trp Gly
850                 855                 860

Asn Ile Ile Val Val Tyr Asn Pro Asn Lys Thr Val Ala Thr Ile Asn
865                 870                 875                 880

Leu Pro Ser Gly Lys Trp Ala Ile Asn Ala Thr Ser Gly Lys Val Gly
            885                 890                 895

Glu Ser Thr Leu Gly Gln Ala Glu Gly Ser Val Gln Val Pro Gly Ile
        900                 905                 910

Ser Met Met Ile Leu His Gln Glu Val Ser Pro Asp His Gly Lys Lys
    915                 920                 925

<210> SEQ ID NO 3
<211> LENGTH: 2589
<212> TYPE: DNA
<213> ORGANISM: Bacillus acidopullulyticus
<220> FEATURE:
<221> NAME/KEY: sig_peptide
<222> LOCATION: (1)..(99)
<220> FEATURE:
<221> NAME/KEY: CDS
<222> LOCATION: (1)..(2586)
<220> FEATURE:
<221> NAME/KEY: mat_peptide
<222> LOCATION: (100)..(2589)

<400> SEQUENCE: 3 atg tcc cta ata cgt tct agg tat aat cat ttt gtc att ctt ttt act    48
Met Ser Leu Ile Arg Ser Arg Tyr Asn His Phe Val Ile Leu Phe Thr
        -30                 -25                 -20 gtc gcc ata atg ttt cta aca gtt tgt ttc ccc gct tat aaa gct tta    96
Val Ala Ile Met Phe Leu Thr Val Cys Phe Pro Ala Tyr Lys Ala Leu
    -15                 -10                 -5 gca gat tct acc tcg aca gaa gtc att gtg cat tat cat cgt ttt gat   144
Ala Asp Ser Thr Ser Thr Glu Val Ile Val His Tyr His Arg Phe Asp
-1  1               5                   10                  15 tct aac tat gca aat tgg gat cta tgg atg tgg cca tat caa cca gtt   192
Ser Asn Tyr Ala Asn Trp Asp Leu Trp Met Trp Pro Tyr Gln Pro Val
            20                  25                  30 aat ggt aat gga gca gca tac gag ttt tct gga aag gat gat ttt ggc   240
Asn Gly Asn Gly Ala Ala Tyr Glu Phe Ser Gly Lys Asp Asp Phe Gly
        35                  40                  45 gtt aaa gca gat gtt caa gtg cct ggg gat gat aca cag gta ggt ctg   288
Val Lys Ala Asp Val Gln Val Pro Gly Asp Asp Thr Gln Val Gly Leu
    50                  55                  60
```

```
att gtc cgt aca aat gat tgg agc caa aaa aat aca tca gac gat ctc      336
Ile Val Arg Thr Asn Asp Trp Ser Gln Lys Asn Thr Ser Asp Asp Leu
    65                  70                  75 cat att gat ctg aca aag ggg cat gaa ata tgg att gtt cag ggg gat      384
His Ile Asp Leu Thr Lys Gly His Glu Ile Trp Ile Val Gln Gly Asp
 80                  85                  90                  95 ccc aat att tat tac aat ctg agt gat gcg cag gct gca gcg act cca      432
Pro Asn Ile Tyr Tyr Asn Leu Ser Asp Ala Gln Ala Ala Ala Thr Pro
                100                 105                 110 aag gtt tcg aat gcg tat ttg gat aat gaa aaa aca gta ttg gca aag      480
Lys Val Ser Asn Ala Tyr Leu Asp Asn Glu Lys Thr Val Leu Ala Lys
            115                 120                 125 cta act aat cca atg aca tta tca gat gga tca agc ggc ttt acg gtt      528
Leu Thr Asn Pro Met Thr Leu Ser Asp Gly Ser Ser Gly Phe Thr Val
        130                 135                 140 aca gat aaa aca aca ggg gaa caa att cca gtt acc gct gca aca aat      576
Thr Asp Lys Thr Thr Gly Glu Gln Ile Pro Val Thr Ala Ala Thr Asn
    145                 150                 155 gcg aac tca gcc tcc tcg tct gag cag aca gac ttg gtt caa ttg acg      624
Ala Asn Ser Ala Ser Ser Ser Glu Gln Thr Asp Leu Val Gln Leu Thr
160                 165                 170                 175 tta gcc agt gca ccg gat gtt tcc cat aca ata caa gta gga gca gcc      672
Leu Ala Ser Ala Pro Asp Val Ser His Thr Ile Gln Val Gly Ala Ala
                180                 185                 190 ggt tat gaa gca gtc aat ctc ata cca cga aat gta tta aat ttg cct      720
Gly Tyr Glu Ala Val Asn Leu Ile Pro Arg Asn Val Leu Asn Leu Pro
            195                 200                 205 cgt tat tat tac agc gga aat gat tta ggt aac gtt tat tca aat aag      768
Arg Tyr Tyr Tyr Ser Gly Asn Asp Leu Gly Asn Val Tyr Ser Asn Lys
        210                 215                 220 gca acg gcc ttc cgt gta tgg gct cca act gct tcg gat gtc caa tta      816
Ala Thr Ala Phe Arg Val Trp Ala Pro Thr Ala Ser Asp Val Gln Leu
    225                 230                 235 ctt tta tac aat agt gaa aca gga cct gta acc aaa cag ctt gaa atg      864
Leu Leu Tyr Asn Ser Glu Thr Gly Pro Val Thr Lys Gln Leu Glu Met
240                 245                 250                 255 caa aag agt gat aac ggt aca tgg aaa ctg aag gtc cct ggt aat ctg      912
Gln Lys Ser Asp Asn Gly Thr Trp Lys Leu Lys Val Pro Gly Asn Leu
                260                 265                 270 aaa aat tgg tat tat ctc tat cag gta acg gtg aat ggg aag aca caa      960
Lys Asn Trp Tyr Tyr Leu Tyr Gln Val Thr Val Asn Gly Lys Thr Gln
            275                 280                 285 aca gcc gtt gac cct tat gtg cgt gct att tca gtc aat gca aca cgt     1008
Thr Ala Val Asp Pro Tyr Val Arg Ala Ile Ser Val Asn Ala Thr Arg
        290                 295                 300 ggt atg ata gtc gat tta gaa gat acg aat cct cct gga tgg aaa gaa     1056
Gly Met Ile Val Asp Leu Glu Asp Thr Asn Pro Pro Gly Trp Lys Glu
    305                 310                 315 gat cat caa cag aca cct gcg aac cca gtg gat gaa gta atc tac gaa     1104
Asp His Gln Gln Thr Pro Ala Asn Pro Val Asp Glu Val Ile Tyr Glu
320                 325                 330                 335 gtg cat gtg cgt gat ttt tcg att gat gct aat tca ggc atg aaa aat     1152
Val His Val Arg Asp Phe Ser Ile Asp Ala Asn Ser Gly Met Lys Asn
                340                 345                 350 aaa ggg aaa tat ctt gcc ttt aca gaa cat ggc aca aaa ggc cct gat     1200
Lys Gly Lys Tyr Leu Ala Phe Thr Glu His Gly Thr Lys Gly Pro Asp
            355                 360                 365 aac gtg aaa acg ggt att gat agt ttg aag gaa tta gga atc aat gct     1248
Asn Val Lys Thr Gly Ile Asp Ser Leu Lys Glu Leu Gly Ile Asn Ala
```

```
                370                 375                 380
gtt caa tta cag ccg att gaa gaa ttt aac agc att gat gaa acc caa      1296
Val Gln Leu Gln Pro Ile Glu Glu Phe Asn Ser Ile Asp Glu Thr Gln
    385                 390                 395 cca aat atg tat aac tgg ggc tat gac cca aga aac tac aac gtc cct      1344
Pro Asn Met Tyr Asn Trp Gly Tyr Asp Pro Arg Asn Tyr Asn Val Pro
400                 405                 410                 415 gaa gga gcg tat gca act aca cca gaa gga acg gct cgc att acc cag      1392
Glu Gly Ala Tyr Ala Thr Thr Pro Glu Gly Thr Ala Arg Ile Thr Gln
                420                 425                 430 tta aag caa ctg att caa agc att cat aaa gat cgg att gct atc aat      1440
Leu Lys Gln Leu Ile Gln Ser Ile His Lys Asp Arg Ile Ala Ile Asn
            435                 440                 445 atg gat gtg gtc tat aac cat acc ttt aac gta gga gtg tct gat ttt      1488
Met Asp Val Val Tyr Asn His Thr Phe Asn Val Gly Val Ser Asp Phe
        450                 455                 460 gat aag att gtt ccg caa tac tat tat cgg aca gac agc gca ggt aat      1536
Asp Lys Ile Val Pro Gln Tyr Tyr Tyr Arg Thr Asp Ser Ala Gly Asn
    465                 470                 475 tat acg aac ggc tca ggt gta ggt aat gaa att gcg acc gag cgt ccg      1584
Tyr Thr Asn Gly Ser Gly Val Gly Asn Glu Ile Ala Thr Glu Arg Pro
480                 485                 490                 495 atg gtc caa aag ttc gtt ctg gat tct gtt aaa tat tgg gta aag gaa      1632
Met Val Gln Lys Phe Val Leu Asp Ser Val Lys Tyr Trp Val Lys Glu
                500                 505                 510 tac cat atc gac ggc ttc cgt ttc gat ctt atg gct ctt tta gga aaa      1680
Tyr His Ile Asp Gly Phe Arg Phe Asp Leu Met Ala Leu Leu Gly Lys
            515                 520                 525 gac acc atg gcc aaa ata tca aaa gag ctt cat gct att aat cct ggc      1728
Asp Thr Met Ala Lys Ile Ser Lys Glu Leu His Ala Ile Asn Pro Gly
        530                 535                 540 att gtc ctg tat gga gaa cca tgg act ggc ggt acc tct gga tta tca      1776
Ile Val Leu Tyr Gly Glu Pro Trp Thr Gly Gly Thr Ser Gly Leu Ser
    545                 550                 555 agc gac caa ctc gtt acg aaa ggt cag caa aag ggc ttg gga att ggc      1824
Ser Asp Gln Leu Val Thr Lys Gly Gln Gln Lys Gly Leu Gly Ile Gly
560                 565                 570                 575 gta ttc aac gat aat att cgg aac gga ctc gat ggt aac gtt ttt gat      1872
Val Phe Asn Asp Asn Ile Arg Asn Gly Leu Asp Gly Asn Val Phe Asp
                580                 585                 590 aaa tcg gca caa gga ttt gca aca gga gat cca aac caa gtt aat gtc      1920
Lys Ser Ala Gln Gly Phe Ala Thr Gly Asp Pro Asn Gln Val Asn Val
            595                 600                 605 att aaa aat gga gtt atg gga agt att tca gat ttc act tcg gca cct      1968
Ile Lys Asn Gly Val Met Gly Ser Ile Ser Asp Phe Thr Ser Ala Pro
        610                 615                 620 agc gaa acc att aac tat gta aca agc cat gat aat atg aca ttg tgg      2016
Ser Glu Thr Ile Asn Tyr Val Thr Ser His Asp Asn Met Thr Leu Trp
    625                 630                 635 gat aaa att agc gca agt aat ccg aac gat aca caa gca gat cga att      2064
Asp Lys Ile Ser Ala Ser Asn Pro Asn Asp Thr Gln Ala Asp Arg Ile
640                 645                 650                 655 aag atg gat gaa ttg gct caa gct gtg gta ttt act tca caa ggg gta      2112
Lys Met Asp Glu Leu Ala Gln Ala Val Val Phe Thr Ser Gln Gly Val
                660                 665                 670 cca ttt atg caa ggt gga gaa gaa atg ctg cgg aca aaa ggc ggt aat      2160
Pro Phe Met Gln Gly Gly Glu Glu Met Leu Arg Thr Lys Gly Gly Asn
            675                 680                 685 gat aat agt tac aat gcc ggg gat agc gtg aat cag ttc gat tgg tca      2208
```

```
Asp Asn Ser Tyr Asn Ala Gly Asp Ser Val Asn Gln Phe Asp Trp Ser
        690                 695                 700 aga aaa gca caa ttt gaa aat gta ttc gac tac tat tct tgg ttg att        2256
Arg Lys Ala Gln Phe Glu Asn Val Phe Asp Tyr Tyr Ser Trp Leu Ile
    705                 710                 715 cat cta cgt gat aat cac cca gca ttc cgt atg acg aca gcg gat caa        2304
His Leu Arg Asp Asn His Pro Ala Phe Arg Met Thr Thr Ala Asp Gln
720                 725                 730                 735 atc aaa caa aat ctc act ttc ttg gat agc cca acg aac act gta gca        2352
Ile Lys Gln Asn Leu Thr Phe Leu Asp Ser Pro Thr Asn Thr Val Ala
                740                 745                 750 ttt gaa tta aaa aat cat gcc aat cat gat aaa tgg aaa aac att ata        2400
Phe Glu Leu Lys Asn His Ala Asn His Asp Lys Trp Lys Asn Ile Ile
            755                 760                 765 gtt atg tat aat cca aat aaa act gca caa act ctc act cta cca agt        2448
Val Met Tyr Asn Pro Asn Lys Thr Ala Gln Thr Leu Thr Leu Pro Ser
        770                 775                 780 gga aat tgg aca att gta gga tta ggc aat caa gta ggt gag aaa tca        2496
Gly Asn Trp Thr Ile Val Gly Leu Gly Asn Gln Val Gly Glu Lys Ser
    785                 790                 795 cta ggc cat gta aat ggc acg gtt gag gtg cca gct ctt agt acg atc        2544
Leu Gly His Val Asn Gly Thr Val Glu Val Pro Ala Leu Ser Thr Ile
800                 805                 810                 815 att ctt cat cag ggt aca tct gaa gat gtc att gat caa aat taa            2589
Ile Leu His Gln Gly Thr Ser Glu Asp Val Ile Asp Gln Asn
                820                 825

<210> SEQ ID NO 4
<211> LENGTH: 862
<212> TYPE: PRT
<213> ORGANISM: Bacillus acidopullulyticus

<400> SEQUENCE: 4

Met Ser Leu Ile Arg Ser Arg Tyr Asn His Phe Val Ile Leu Phe Thr
            -30                 -25                 -20

Val Ala Ile Met Phe Leu Thr Val Cys Phe Pro Ala Tyr Lys Ala Leu
        -15                 -10                  -5

Ala Asp Ser Thr Ser Thr Glu Val Ile Val His Tyr His Arg Phe Asp
 -1   1               5                  10                  15

Ser Asn Tyr Ala Asn Trp Asp Leu Trp Met Trp Pro Tyr Gln Pro Val
                20                  25                  30

Asn Gly Asn Gly Ala Ala Tyr Glu Phe Ser Gly Lys Asp Asp Phe Gly
            35                  40                  45

Val Lys Ala Asp Val Gln Val Pro Gly Asp Asp Thr Gln Val Gly Leu
        50                  55                  60

Ile Val Arg Thr Asn Asp Trp Ser Gln Lys Asn Thr Ser Asp Asp Leu
    65                  70                  75

His Ile Asp Leu Thr Lys Gly His Glu Ile Trp Ile Val Gln Gly Asp
80                  85                  90                  95

Pro Asn Ile Tyr Tyr Asn Leu Ser Asp Ala Gln Ala Ala Thr Pro
                100                 105                 110

Lys Val Ser Asn Ala Tyr Leu Asp Asn Glu Lys Thr Val Leu Ala Lys
            115                 120                 125

Leu Thr Asn Pro Met Thr Leu Ser Asp Gly Ser Ser Gly Phe Thr Val
        130                 135                 140

Thr Asp Lys Thr Thr Gly Glu Gln Ile Pro Val Thr Ala Ala Thr Asn
    145                 150                 155
```

```
Ala Asn Ser Ala Ser Ser Glu Gln Thr Asp Leu Val Gln Leu Thr
160                 165                 170                 175

Leu Ala Ser Ala Pro Asp Val Ser His Thr Ile Gln Val Gly Ala Ala
                180                 185                 190

Gly Tyr Glu Ala Val Asn Leu Ile Pro Arg Asn Val Leu Asn Leu Pro
            195                 200                 205

Arg Tyr Tyr Ser Gly Asn Asp Leu Gly Asn Val Tyr Ser Asn Lys
        210                 215                 220

Ala Thr Ala Phe Arg Val Trp Ala Pro Thr Ala Ser Asp Val Gln Leu
    225                 230                 235

Leu Leu Tyr Asn Ser Glu Thr Gly Pro Val Thr Lys Gln Leu Glu Met
240                 245                 250                 255

Gln Lys Ser Asp Asn Gly Thr Trp Lys Leu Lys Val Pro Gly Asn Leu
                260                 265                 270

Lys Asn Trp Tyr Tyr Leu Tyr Gln Val Thr Val Asn Gly Lys Thr Gln
            275                 280                 285

Thr Ala Val Asp Pro Tyr Val Arg Ala Ile Ser Val Asn Ala Thr Arg
        290                 295                 300

Gly Met Ile Val Asp Leu Glu Asp Thr Asn Pro Pro Gly Trp Lys Glu
    305                 310                 315

Asp His Gln Gln Thr Pro Ala Asn Pro Val Asp Glu Val Ile Tyr Glu
320                 325                 330                 335

Val His Val Arg Asp Phe Ser Ile Asp Ala Asn Ser Gly Met Lys Asn
                340                 345                 350

Lys Gly Lys Tyr Leu Ala Phe Thr Glu His Gly Thr Lys Gly Pro Asp
            355                 360                 365

Asn Val Lys Thr Gly Ile Asp Ser Leu Lys Glu Leu Gly Ile Asn Ala
        370                 375                 380

Val Gln Leu Gln Pro Ile Glu Glu Phe Asn Ser Ile Asp Glu Thr Gln
    385                 390                 395

Pro Asn Met Tyr Asn Trp Gly Tyr Asp Pro Arg Asn Tyr Asn Val Pro
400                 405                 410                 415

Glu Gly Ala Tyr Ala Thr Thr Pro Glu Gly Thr Ala Arg Ile Thr Gln
                420                 425                 430

Leu Lys Gln Leu Ile Gln Ser Ile His Lys Asp Arg Ile Ala Ile Asn
            435                 440                 445

Met Asp Val Val Tyr Asn His Thr Phe Asn Val Gly Val Ser Asp Phe
        450                 455                 460

Asp Lys Ile Val Pro Gln Tyr Tyr Arg Thr Asp Ser Ala Gly Asn
    465                 470                 475

Tyr Thr Asn Gly Ser Gly Val Gly Asn Glu Ile Ala Thr Glu Arg Pro
480                 485                 490                 495

Met Val Gln Lys Phe Val Leu Asp Ser Val Lys Tyr Trp Val Lys Glu
                500                 505                 510

Tyr His Ile Asp Gly Phe Arg Phe Asp Leu Met Ala Leu Leu Gly Lys
            515                 520                 525

Asp Thr Met Ala Lys Ile Ser Lys Glu Leu His Ala Ile Asn Pro Gly
        530                 535                 540

Ile Val Leu Tyr Gly Glu Pro Trp Thr Gly Gly Thr Ser Gly Leu Ser
    545                 550                 555

Ser Asp Gln Leu Val Thr Lys Gly Gln Gln Lys Gly Leu Gly Ile Gly
560                 565                 570                 575

Val Phe Asn Asp Asn Ile Arg Asn Gly Leu Asp Gly Asn Val Phe Asp
```

```
                        580                 585                 590
Lys Ser Ala Gln Gly Phe Ala Thr Gly Asp Pro Asn Gln Val Asn Val
                595                 600                 605

Ile Lys Asn Gly Val Met Gly Ser Ile Ser Asp Phe Thr Ser Ala Pro
                610                 615                 620

Ser Glu Thr Ile Asn Tyr Val Thr Ser His Asp Asn Met Thr Leu Trp
            625                 630                 635

Asp Lys Ile Ser Ala Ser Asn Pro Asn Asp Thr Gln Ala Asp Arg Ile
640                 645                 650                 655

Lys Met Asp Glu Leu Ala Gln Ala Val Val Phe Thr Ser Gln Gly Val
                660                 665                 670

Pro Phe Met Gln Gly Gly Glu Met Leu Arg Thr Lys Gly Gly Asn
            675                 680                 685

Asp Asn Ser Tyr Asn Ala Gly Asp Ser Val Asn Gln Phe Asp Trp Ser
                690                 695                 700

Arg Lys Ala Gln Phe Glu Asn Val Phe Asp Tyr Tyr Ser Trp Leu Ile
            705                 710                 715

His Leu Arg Asp Asn His Pro Ala Phe Arg Met Thr Thr Ala Asp Gln
720                 725                 730                 735

Ile Lys Gln Asn Leu Thr Phe Leu Asp Ser Pro Thr Asn Thr Val Ala
                740                 745                 750

Phe Glu Leu Lys Asn His Ala Asn His Asp Lys Trp Lys Asn Ile Ile
            755                 760                 765

Val Met Tyr Asn Pro Asn Lys Thr Ala Gln Thr Leu Thr Leu Pro Ser
                770                 775                 780

Gly Asn Trp Thr Ile Val Gly Leu Gly Asn Gln Val Gly Glu Lys Ser
            785                 790                 795

Leu Gly His Val Asn Gly Thr Val Glu Val Pro Ala Leu Ser Thr Ile
800                 805                 810                 815

Ile Leu His Gln Gly Thr Ser Glu Asp Val Ile Asp Gln Asn
                820                 825

<210> SEQ ID NO 5
<211> LENGTH: 2589
<212> TYPE: DNA
<213> ORGANISM: Bacillus acidopullulyticus
<220> FEATURE:
<221> NAME/KEY: CDS
<222> LOCATION: (1)..(2586)
<220> FEATURE:
<221> NAME/KEY: sig_peptide
<222> LOCATION: (1)..(99)
<220> FEATURE:
<221> NAME/KEY: mat_peptide
<222> LOCATION: (100)..(2586)

<400> SEQUENCE: 5 gtg tcc cta ata cgt tct agg tat aat cat ttt gtc att ctt ttt act    48
Val Ser Leu Ile Arg Ser Arg Tyr Asn His Phe Val Ile Leu Phe Thr
            -30                 -25                 -20 gtc gcc ata atg ttt cta aca gtt tgt ttc ccc gct tat aaa gct tta    96
Val Ala Ile Met Phe Leu Thr Val Cys Phe Pro Ala Tyr Lys Ala Leu
        -15                 -10                  -5 gca gat tct acc tcg aca gaa gtc att gtg cat tat cat cgt ttt gat   144
Ala Asp Ser Thr Ser Thr Glu Val Ile Val His Tyr His Arg Phe Asp
 -1   1               5                  10                  15 tct aac tat gca aat tgg gat cta tgg atg tgg cca tat caa cca gtt   192
Ser Asn Tyr Ala Asn Trp Asp Leu Trp Met Trp Pro Tyr Gln Pro Val
                 20                  25                  30
```

-continued

| | |
|---|---|
| aat ggt aat gga gca gca tac gag ttt tct gga aag gat gat ttt ggc<br>Asn Gly Asn Gly Ala Ala Tyr Glu Phe Ser Gly Lys Asp Asp Phe Gly<br>           35                      40                     45 | 240 |
| gtt aaa gca gat gtt caa gtg cct ggg gat gat aca cag gta ggt ctg<br>Val Lys Ala Asp Val Gln Val Pro Gly Asp Asp Thr Gln Val Gly Leu<br>      50                     55                      60 | 288 |
| att gtc cgt aca aat gat tgg agc caa aaa aat aca tca gac gat ctc<br>Ile Val Arg Thr Asn Asp Trp Ser Gln Lys Asn Thr Ser Asp Asp Leu<br> 65                     70                      75 | 336 |
| cat att gat ctg aca aag ggg cat gaa ata tgg att gtt cag ggg gat<br>His Ile Asp Leu Thr Lys Gly His Glu Ile Trp Ile Val Gln Gly Asp<br>80                 85                     90                     95 | 384 |
| ccc aat att tat tac aat ctg agt gat gcg cag gct gca gcg act cca<br>Pro Asn Ile Tyr Tyr Asn Leu Ser Asp Ala Gln Ala Ala Ala Thr Pro<br>               100                   105                  110 | 432 |
| aag gtt tcg aat gcg tat ttg gat aat gaa aaa aca gta ttg gca aag<br>Lys Val Ser Asn Ala Tyr Leu Asp Asn Glu Lys Thr Val Leu Ala Lys<br>            115                   120                  125 | 480 |
| cta act aat cca atg aca tta tca gat gga tca agc ggc ttt acg gtt<br>Leu Thr Asn Pro Met Thr Leu Ser Asp Gly Ser Ser Gly Phe Thr Val<br>      130                   135                     140 | 528 |
| aca gat aaa aca aca ggg gaa caa att cca gtt acc gct gca aca aat<br>Thr Asp Lys Thr Thr Gly Glu Gln Ile Pro Val Thr Ala Ala Thr Asn<br>145                 150                   155 | 576 |
| gcg aac tca gcc tcc tcg tct gag cag aca gac ttg gtt caa ttg acg<br>Ala Asn Ser Ala Ser Ser Ser Glu Gln Thr Asp Leu Val Gln Leu Thr<br>160                 165                   170                  175 | 624 |
| tta gcc agt gca ccg gat gtt tcc cat aca ata caa gta gga gca gcc<br>Leu Ala Ser Ala Pro Asp Val Ser His Thr Ile Gln Val Gly Ala Ala<br>               180                   185                  190 | 672 |
| ggt tat gaa gca gtc aat ctc ata cca cga aat gta tta aat ttg cct<br>Gly Tyr Glu Ala Val Asn Leu Ile Pro Arg Asn Val Leu Asn Leu Pro<br>            195                   200                  205 | 720 |
| cgt tat tat tac agc gga aat gat tta ggt aac gtt tat tca aat aag<br>Arg Tyr Tyr Tyr Ser Gly Asn Asp Leu Gly Asn Val Tyr Ser Asn Lys<br>      210                   215                     220 | 768 |
| gca acg gcc ttc cgt gta tgg gct cca act gct tcg gat gtc caa tta<br>Ala Thr Ala Phe Arg Val Trp Ala Pro Thr Ala Ser Asp Val Gln Leu<br>225                 230                   235 | 816 |
| ctt tta tac aat agt gaa aca gga cct gta acc aaa cag ctt gaa atg<br>Leu Leu Tyr Asn Ser Glu Thr Gly Pro Val Thr Lys Gln Leu Glu Met<br>240                 245                   250                  255 | 864 |
| caa aag agt gat aac ggt aca tgg aaa ctg aag gtc cct ggt aat ctg<br>Gln Lys Ser Asp Asn Gly Thr Trp Lys Leu Lys Val Pro Gly Asn Leu<br>            260                   265                  270 | 912 |
| aaa aat tgg tat tat ctc tat cag gta acg gtg aat ggg aag aca caa<br>Lys Asn Trp Tyr Tyr Leu Tyr Gln Val Thr Val Asn Gly Lys Thr Gln<br>               275                   280                  285 | 960 |
| aca gcc gtt gac cct tat gtg cgt gct att tca gtc aat gca aca cgt<br>Thr Ala Val Asp Pro Tyr Val Arg Ala Ile Ser Val Asn Ala Thr Arg<br>      290                   295                     300 | 1008 |
| ggt atg ata gtc gat tta gaa gat acg aat cct cct gga tgg aaa gaa<br>Gly Met Ile Val Asp Leu Glu Asp Thr Asn Pro Pro Gly Trp Lys Glu<br>305                 310                   315 | 1056 |
| gat cat caa cag aca cct gcg aac cca gtg gat gaa gta atc tac gaa<br>Asp His Gln Gln Thr Pro Ala Asn Pro Val Asp Glu Val Ile Tyr Glu<br>320                 325                   330                  335 | 1104 |
| gtg cat gtg cgt gat ttt tcg att gat gct aat tca ggc atg aaa aat<br>Val His Val Arg Asp Phe Ser Ile Asp Ala Asn Ser Gly Met Lys Asn | 1152 |

```
                   340                 345                 350
aaa ggg aaa tat ctt gcc ttt aca gaa cat ggc aca aaa ggc cct gat    1200
Lys Gly Lys Tyr Leu Ala Phe Thr Glu His Gly Thr Lys Gly Pro Asp
            355                 360                 365 aac gtg aaa acg ggt att gat agt ttg aag gaa tta gga atc aat gct    1248
Asn Val Lys Thr Gly Ile Asp Ser Leu Lys Glu Leu Gly Ile Asn Ala
        370                 375                 380 gtt caa tta cag ccg att gaa gaa ttt aac agc att gat gaa acc caa    1296
Val Gln Leu Gln Pro Ile Glu Glu Phe Asn Ser Ile Asp Glu Thr Gln
385                 390                 395 cca aat atg tat aac tgg ggc tat gac cca aga aac tac aac gtc cct    1344
Pro Asn Met Tyr Asn Trp Gly Tyr Asp Pro Arg Asn Tyr Asn Val Pro
400                 405                 410                 415 gaa gga gcg tat gca act aca cca gaa gga acg gct cgc att acc cag    1392
Glu Gly Ala Tyr Ala Thr Thr Pro Glu Gly Thr Ala Arg Ile Thr Gln
                420                 425                 430 tta aag caa ctg att caa agc att cat aaa gat cgg att gct atc aat    1440
Leu Lys Gln Leu Ile Gln Ser Ile His Lys Asp Arg Ile Ala Ile Asn
            435                 440                 445 atg gat gtg gtc tat aac cat acc ttt aac gta gga gtg tct gat ttt    1488
Met Asp Val Val Tyr Asn His Thr Phe Asn Val Gly Val Ser Asp Phe
        450                 455                 460 gat aag att gtt ccg caa tac tat tat cgg aca gac agc gca ggt aat    1536
Asp Lys Ile Val Pro Gln Tyr Tyr Tyr Arg Thr Asp Ser Ala Gly Asn
465                 470                 475 tat acg aac ggc tca ggt gta ggt aat gaa att gcg acc gag cgt ccg    1584
Tyr Thr Asn Gly Ser Gly Val Gly Asn Glu Ile Ala Thr Glu Arg Pro
480                 485                 490                 495 atg gtc caa aag ttc gtt ctg gat tct gtt aaa tat tgg gta aag gaa    1632
Met Val Gln Lys Phe Val Leu Asp Ser Val Lys Tyr Trp Val Lys Glu
                500                 505                 510 tac cat atc gac ggc ttc cgt ttc gat ctt atg gct ctt tta gga aaa    1680
Tyr His Ile Asp Gly Phe Arg Phe Asp Leu Met Ala Leu Leu Gly Lys
            515                 520                 525 gac acc atg gcc aaa ata tca aaa gag ctt cat gct att aat cct ggc    1728
Asp Thr Met Ala Lys Ile Ser Lys Glu Leu His Ala Ile Asn Pro Gly
        530                 535                 540 att gtc ctg tat gga gaa cca tgg act ggc ggt acc tct gga tta tca    1776
Ile Val Leu Tyr Gly Glu Pro Trp Thr Gly Gly Thr Ser Gly Leu Ser
545                 550                 555 agc gac caa ctc gtt acg aaa ggt cag caa aag ggc ttg gga att ggc    1824
Ser Asp Gln Leu Val Thr Lys Gly Gln Gln Lys Gly Leu Gly Ile Gly
560                 565                 570                 575 gta ttc aac gat aat att cgg aac gga ctc gat ggt aac gtt ttt gat    1872
Val Phe Asn Asp Asn Ile Arg Asn Gly Leu Asp Gly Asn Val Phe Asp
                580                 585                 590 aaa tcg gca caa gga ttt gca aca gga gat cca aac caa gtt aat gtc    1920
Lys Ser Ala Gln Gly Phe Ala Thr Gly Asp Pro Asn Gln Val Asn Val
            595                 600                 605 att aaa aat aga gtt atg gga agt att tca gat ttc act tcg gca cct    1968
Ile Lys Asn Arg Val Met Gly Ser Ile Ser Asp Phe Thr Ser Ala Pro
        610                 615                 620 agc gaa acc att aac tat gta aca agc cat gat aat atg aca ttg tgg    2016
Ser Glu Thr Ile Asn Tyr Val Thr Ser His Asp Asn Met Thr Leu Trp
625                 630                 635 gat aaa att agc gca agt aat ccg aac gat aca caa gca gat cga att    2064
Asp Lys Ile Ser Ala Ser Asn Pro Asn Asp Thr Gln Ala Asp Arg Ile
640                 645                 650                 655 aag atg gat gaa ttg gct caa gct gtg gta ttt act tca caa ggg gta    2112
```

```
                Lys Met Asp Glu Leu Ala Gln Ala Val Val Phe Thr Ser Gln Gly Val
                            660                 665                 670 cca ttt atg caa ggt gga gaa gaa atg ctg cgg aca aaa ggc ggt aat              2160
Pro Phe Met Gln Gly Gly Glu Glu Met Leu Arg Thr Lys Gly Gly Asn
                675                 680                 685 gat aat agt tac aat gcc ggg gat agc gtg aat cag ttc gat tgg tca              2208
Asp Asn Ser Tyr Asn Ala Gly Asp Ser Val Asn Gln Phe Asp Trp Ser
                690                 695                 700 aga aaa gca caa ttt gaa aat gta ttc gac tac tat tct tgg ttg att              2256
Arg Lys Ala Gln Phe Glu Asn Val Phe Asp Tyr Tyr Ser Trp Leu Ile
            705                 710                 715 cat cta cgt gat aat cac cca gca ttc cgt atg acg aca gcg gat caa              2304
His Leu Arg Asp Asn His Pro Ala Phe Arg Met Thr Thr Ala Asp Gln
        720                 725                 730                 735 atc aaa caa aat ctc act ttc ttg gat agc cca acg aac act gta gca              2352
Ile Lys Gln Asn Leu Thr Phe Leu Asp Ser Pro Thr Asn Thr Val Ala
                    740                 745                 750 ttt gaa tta aaa aat cat gcc aat cat gat aaa tgg aaa aac att ata              2400
Phe Glu Leu Lys Asn His Ala Asn His Asp Lys Trp Lys Asn Ile Ile
                755                 760                 765 gtt atg tat aat cca aat aaa act gca caa act ctc act cta cca agt              2448
Val Met Tyr Asn Pro Asn Lys Thr Ala Gln Thr Leu Thr Leu Pro Ser
            770                 775                 780 gga aat tgg aca att gta gga tta ggc aat caa gta ggt gag aaa tca              2496
Gly Asn Trp Thr Ile Val Gly Leu Gly Asn Gln Val Gly Glu Lys Ser
        785                 790                 795 cta ggc cat gta aat ggc acg gtt gag gtg cca gct ctt agt acg atc              2544
Leu Gly His Val Asn Gly Thr Val Glu Val Pro Ala Leu Ser Thr Ile
800                 805                 810                 815 att ctt cat cag ggt aca tct gaa gat gtc att gat caa aat taa                  2589
Ile Leu His Gln Gly Thr Ser Glu Asp Val Ile Asp Gln Asn
                    820                 825

<210> SEQ ID NO 6
<211> LENGTH: 862
<212> TYPE: PRT
<213> ORGANISM: Bacillus acidopullulyticus

<400> SEQUENCE: 6

Val Ser Leu Ile Arg Ser Arg Tyr Asn His Phe Val Ile Leu Phe Thr
            -30                 -25                 -20

Val Ala Ile Met Phe Leu Thr Val Cys Phe Pro Ala Tyr Lys Ala Leu
        -15                 -10                 -5

Ala Asp Ser Thr Ser Thr Glu Val Ile Val His Tyr His Arg Phe Asp
-1  1                   5                   10                  15

Ser Asn Tyr Ala Asn Trp Asp Leu Trp Met Trp Pro Tyr Gln Pro Val
                20                  25                  30

Asn Gly Asn Gly Ala Ala Tyr Glu Phe Ser Gly Lys Asp Asp Phe Gly
            35                  40                  45

Val Lys Ala Asp Val Gln Val Pro Gly Asp Thr Gln Val Gly Leu
        50                  55                  60

Ile Val Arg Thr Asn Asp Trp Ser Gln Lys Asn Thr Ser Asp Asp Leu
    65                  70                  75

His Ile Asp Leu Thr Lys Gly His Glu Ile Trp Ile Val Gln Gly Asp
80                  85                  90                  95

Pro Asn Ile Tyr Tyr Asn Leu Ser Asp Ala Gln Ala Ala Ala Thr Pro
                100                 105                 110

Lys Val Ser Asn Ala Tyr Leu Asp Asn Glu Lys Thr Val Leu Ala Lys
```

```
                    115                 120                 125
Leu Thr Asn Pro Met Thr Leu Ser Asp Gly Ser Ser Phe Thr Val
            130                 135                 140
Thr Asp Lys Thr Thr Gly Glu Gln Ile Pro Val Thr Ala Thr Asn
        145                 150                 155
Ala Asn Ser Ala Ser Ser Glu Gln Thr Asp Leu Val Gln Leu Thr
160                 165                 170                 175
Leu Ala Ser Ala Pro Asp Val Ser His Thr Ile Gln Val Gly Ala Ala
                180                 185                 190
Gly Tyr Glu Ala Val Asn Leu Ile Pro Arg Asn Val Leu Asn Leu Pro
            195                 200                 205
Arg Tyr Tyr Ser Gly Asn Asp Leu Gly Asn Val Tyr Ser Asn Lys
        210                 215                 220
Ala Thr Ala Phe Arg Val Trp Ala Pro Thr Ala Ser Asp Val Gln Leu
    225                 230                 235
Leu Leu Tyr Asn Ser Glu Thr Gly Pro Val Thr Lys Gln Leu Glu Met
240                 245                 250                 255
Gln Lys Ser Asp Asn Gly Thr Trp Lys Leu Lys Val Pro Gly Asn Leu
                260                 265                 270
Lys Asn Trp Tyr Tyr Leu Tyr Gln Val Thr Val Asn Gly Lys Thr Gln
            275                 280                 285
Thr Ala Val Asp Pro Tyr Val Arg Ala Ile Ser Val Asn Ala Thr Arg
        290                 295                 300
Gly Met Ile Val Asp Leu Glu Asp Thr Asn Pro Pro Gly Trp Lys Glu
    305                 310                 315
Asp His Gln Gln Thr Pro Ala Asn Pro Val Asp Glu Val Ile Tyr Glu
320                 325                 330                 335
Val His Val Arg Asp Phe Ser Ile Asp Ala Asn Ser Gly Met Lys Asn
                340                 345                 350
Lys Gly Lys Tyr Leu Ala Phe Thr Glu His Gly Thr Lys Gly Pro Asp
            355                 360                 365
Asn Val Lys Thr Gly Ile Asp Ser Leu Lys Glu Leu Gly Ile Asn Ala
        370                 375                 380
Val Gln Leu Gln Pro Ile Glu Glu Phe Asn Ser Ile Asp Glu Thr Gln
    385                 390                 395
Pro Asn Met Tyr Asn Trp Gly Tyr Asp Pro Arg Asn Tyr Asn Val Pro
400                 405                 410                 415
Glu Gly Ala Tyr Ala Thr Thr Pro Glu Gly Thr Ala Arg Ile Thr Gln
                420                 425                 430
Leu Lys Gln Leu Ile Gln Ser Ile His Lys Asp Arg Ile Ala Ile Asn
            435                 440                 445
Met Asp Val Val Tyr Asn His Thr Phe Asn Val Gly Val Ser Asp Phe
        450                 455                 460
Asp Lys Ile Val Pro Gln Tyr Tyr Arg Thr Asp Ser Ala Gly Asn
    465                 470                 475
Tyr Thr Asn Gly Ser Gly Val Gly Asn Glu Ile Ala Thr Glu Arg Pro
480                 485                 490                 495
Met Val Gln Lys Phe Val Leu Asp Ser Val Lys Tyr Trp Val Lys Glu
                500                 505                 510
Tyr His Ile Asp Gly Phe Arg Phe Asp Leu Met Ala Leu Leu Gly Lys
            515                 520                 525
Asp Thr Met Ala Lys Ile Ser Lys Glu Leu His Ala Ile Asn Pro Gly
        530                 535                 540
```

```
Ile Val Leu Tyr Gly Glu Pro Trp Thr Gly Thr Ser Gly Leu Ser
    545                 550                 555

Ser Asp Gln Leu Val Thr Lys Gly Gln Gln Lys Gly Leu Gly Ile Gly
560                 565                 570                 575

Val Phe Asn Asp Asn Ile Arg Asn Gly Leu Asp Gly Asn Val Phe Asp
                580                 585                 590

Lys Ser Ala Gln Gly Phe Ala Thr Gly Asp Pro Asn Gln Val Asn Val
                595                 600                 605

Ile Lys Asn Arg Val Met Gly Ser Ile Ser Asp Phe Thr Ser Ala Pro
                610                 615                 620

Ser Glu Thr Ile Asn Tyr Val Thr Ser His Asp Asn Met Thr Leu Trp
                625                 630                 635

Asp Lys Ile Ser Ala Ser Asn Pro Asn Asp Thr Gln Ala Asp Arg Ile
640                 645                 650                 655

Lys Met Asp Glu Leu Ala Gln Ala Val Val Phe Thr Ser Gln Gly Val
                660                 665                 670

Pro Phe Met Gln Gly Gly Glu Glu Met Leu Arg Thr Lys Gly Gly Asn
                675                 680                 685

Asp Asn Ser Tyr Asn Ala Gly Asp Ser Val Asn Gln Phe Asp Trp Ser
                690                 695                 700

Arg Lys Ala Gln Phe Glu Asn Val Phe Asp Tyr Tyr Ser Trp Leu Ile
                705                 710                 715

His Leu Arg Asp Asn His Pro Ala Phe Arg Met Thr Thr Ala Asp Gln
720                 725                 730                 735

Ile Lys Gln Asn Leu Thr Phe Leu Asp Ser Pro Thr Asn Thr Val Ala
                740                 745                 750

Phe Glu Leu Lys Asn His Ala Asn His Asp Lys Trp Lys Asn Ile Ile
                755                 760                 765

Val Met Tyr Asn Pro Asn Lys Thr Ala Gln Thr Leu Thr Leu Pro Ser
                770                 775                 780

Gly Asn Trp Thr Ile Val Gly Leu Gly Asn Gln Val Gly Glu Lys Ser
                785                 790                 795

Leu Gly His Val Asn Gly Thr Val Glu Val Pro Ala Leu Ser Thr Ile
800                 805                 810                 815

Ile Leu His Gln Gly Thr Ser Glu Asp Val Ile Asp Gln Asn
                820                 825

<210> SEQ ID NO 7
<211> LENGTH: 483
<212> TYPE: PRT
<213> ORGANISM: Bacillus licheniformis
<220> FEATURE:
<221> NAME/KEY: mat_peptide
<222> LOCATION: (1)..(483)

<400> SEQUENCE: 7

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
                20                  25                  30

Ala Glu His Gly Ile Thr Ala Val Trp Ile Pro Pro Ala Tyr Lys Gly
                35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
```

-continued

```
            65                  70                  75                  80
Gly Glu Leu Gln Ser Ala Ile Lys Ser Leu His Ser Arg Asp Ile Asn
                    85                  90                  95
Val Tyr Gly Asp Val Val Ile Asn His Lys Gly Gly Ala Asp Ala Thr
                100                 105                 110
Glu Asp Val Thr Ala Val Glu Val Asp Pro Ala Asp Arg Asn Arg Val
                115                 120                 125
Ile Ser Gly Glu His Leu Ile Lys Ala Trp Thr His Phe His Phe Pro
        130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                    165                 170                 175
Phe Gln Gly Lys Ala Trp Asp Trp Glu Val Ser Asn Glu Asn Gly Asn
                180                 185                 190
Tyr Asp Tyr Leu Met Tyr Ala Asp Ile Asp Tyr Asp His Pro Asp Val
                195                 200                 205
Ala Ala Glu Ile Lys Arg Trp Gly Thr Trp Tyr Ala Asn Glu Leu Gln
        210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                    245                 250                 255
Phe Thr Val Ala Glu Tyr Trp Gln Asn Asp Leu Gly Ala Leu Glu Asn
                260                 265                 270
Tyr Leu Asn Lys Thr Asn Phe Asn His Ser Val Phe Asp Val Pro Leu
                275                 280                 285
His Tyr Gln Phe His Ala Ala Ser Thr Gln Gly Gly Tyr Asp Met
        290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                    325                 330                 335
Ser Thr Val Gln Thr Trp Phe Lys Pro Leu Ala Tyr Ala Phe Ile Leu
                340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
    370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                    405                 410                 415
Ser Ser Val Ala Asn Ser Gly Leu Ala Ala Leu Ile Thr Asp Gly Pro
                420                 425                 430
Gly Gly Ala Lys Arg Met Tyr Val Gly Arg Gln Asn Ala Gly Glu Thr
        435                 440                 445
Trp His Asp Ile Thr Gly Asn Arg Ser Glu Pro Val Val Ile Asn Ser
    450                 455                 460
Glu Gly Trp Gly Glu Phe His Val Asn Gly Gly Ser Val Ser Ile Tyr
465                 470                 475                 480

Val Gln Arg
```

-continued

```
<210> SEQ ID NO 8
<211> LENGTH: 2160
<212> TYPE: DNA
<213> ORGANISM: Bacillus sp.
<220> FEATURE:
<221> NAME/KEY: CDS
<222> LOCATION: (1)..(2157)
<220> FEATURE:
<221> NAME/KEY: mat_peptide
<222> LOCATION: (100)..(2157)

<400> SEQUENCE: 8
```

| | | | | | | | | | | | | | | | | |
|---|---|---|---|---|---|---|---|---|---|---|---|---|---|---|---|---|
| atg | aaa | aag | aaa | acg | ctt | tct | tta | ttt | gtg | gga | ctg | atg | ctc | ctc | atc | 48 |
| Met | Lys | Lys | Lys | Thr | Leu | Ser | Leu | Phe | Val | Gly | Leu | Met | Leu | Leu | Ile | |
| | | | -30 | | | | -25 | | | | | -20 | | | | |
| ggt | ctt | ctg | ttc | agc | ggt | tct | ctt | ccg | tac | aat | cca | aac | gcc | gct | gaa | 96 |
| Gly | Leu | Leu | Phe | Ser | Gly | Ser | Leu | Pro | Tyr | Asn | Pro | Asn | Ala | Ala | Glu | |
| | | -15 | | | | | -10 | | | | | -5 | | | | |
| gcc | agc | agt | tcc | gca | agc | gtc | aaa | ggg | gac | gtg | att | tac | cag | att | atc | 144 |
| Ala | Ser | Ser | Ser | Ala | Ser | Val | Lys | Gly | Asp | Val | Ile | Tyr | Gln | Ile | Ile | |
| -1 | 1 | | | | 5 | | | | | 10 | | | | | 15 | |
| att | gac | cgg | ttt | tac | gat | ggg | gac | acg | acg | aac | aac | aat | cct | gcc | aaa | 192 |
| Ile | Asp | Arg | Phe | Tyr | Asp | Gly | Asp | Thr | Thr | Asn | Asn | Asn | Pro | Ala | Lys | |
| | | | | 20 | | | | | 25 | | | | | 30 | | |
| agt | tat | gga | ctt | tac | gat | ccg | acc | aaa | tcg | aag | tgg | aaa | atg | tat | tgg | 240 |
| Ser | Tyr | Gly | Leu | Tyr | Asp | Pro | Thr | Lys | Ser | Lys | Trp | Lys | Met | Tyr | Trp | |
| | | 35 | | | | | 40 | | | | | 45 | | | | |
| ggc | ggg | gat | ctg | gag | ggg | gtt | cgt | caa | aaa | ctt | cct | tat | ctt | aaa | cag | 288 |
| Gly | Gly | Asp | Leu | Glu | Gly | Val | Arg | Gln | Lys | Leu | Pro | Tyr | Leu | Lys | Gln | |
| | 50 | | | | | 55 | | | | | 60 | | | | | |
| ctg | ggc | gta | acg | aca | atc | tgg | ttg | tcc | ccg | gtt | ttg | gac | aat | ctg | gat | 336 |
| Leu | Gly | Val | Thr | Thr | Ile | Trp | Leu | Ser | Pro | Val | Leu | Asp | Asn | Leu | Asp | |
| 65 | | | | | 70 | | | | | 75 | | | | | | |
| aca | ctg | gcg | ggc | acc | gat | aac | acg | ggc | tat | cac | gga | tac | tgg | acg | cgc | 384 |
| Thr | Leu | Ala | Gly | Thr | Asp | Asn | Thr | Gly | Tyr | His | Gly | Tyr | Trp | Thr | Arg | |
| 80 | | | | | 85 | | | | | 90 | | | | | 95 | |
| gat | ttt | aaa | cag | att | gag | gaa | cat | ttc | ggg | aat | tgg | acc | aca | ttt | gac | 432 |
| Asp | Phe | Lys | Gln | Ile | Glu | Glu | His | Phe | Gly | Asn | Trp | Thr | Thr | Phe | Asp | |
| | | | | 100 | | | | | 105 | | | | | 110 | | |
| acg | ttg | gtc | aat | gat | gct | cac | caa | aac | gga | atc | aag | gtg | att | gtc | gac | 480 |
| Thr | Leu | Val | Asn | Asp | Ala | His | Gln | Asn | Gly | Ile | Lys | Val | Ile | Val | Asp | |
| | | 115 | | | | | 120 | | | | | 125 | | | | |
| ttt | gtg | ccc | aat | cat | tcg | act | cct | ttt | aag | gca | aac | gat | tcc | acc | ttt | 528 |
| Phe | Val | Pro | Asn | His | Ser | Thr | Pro | Phe | Lys | Ala | Asn | Asp | Ser | Thr | Phe | |
| | 130 | | | | | 135 | | | | | 140 | | | | | |
| gcg | gaa | ggc | ggc | gcc | ctc | tac | aac | aat | gga | acc | tat | atg | ggc | aat | tat | 576 |
| Ala | Glu | Gly | Gly | Ala | Leu | Tyr | Asn | Asn | Gly | Thr | Tyr | Met | Gly | Asn | Tyr | |
| 145 | | | | | 150 | | | | | 155 | | | | | | |
| ttt | gat | gac | gca | aca | aaa | ggg | tac | ttc | cac | cat | aat | ggg | gac | atc | agc | 624 |
| Phe | Asp | Asp | Ala | Thr | Lys | Gly | Tyr | Phe | His | His | Asn | Gly | Asp | Ile | Ser | |
| 160 | | | | 165 | | | | | 170 | | | | | 175 | | |
| aac | tgg | gac | gac | cgg | tac | gag | gcg | caa | tgg | aaa | aac | ttc | acg | gat | cca | 672 |
| Asn | Trp | Asp | Asp | Arg | Tyr | Glu | Ala | Gln | Trp | Lys | Asn | Phe | Thr | Asp | Pro | |
| | | | 180 | | | | | 185 | | | | | 190 | | | |
| gcc | ggt | ttc | tcg | ctt | gcc | gat | ttg | tcg | cag | gaa | aat | ggc | acg | att | gct | 720 |
| Ala | Gly | Phe | Ser | Leu | Ala | Asp | Leu | Ser | Gln | Glu | Asn | Gly | Thr | Ile | Ala | |
| | | 195 | | | | | 200 | | | | | 205 | | | | |
| caa | tac | ctg | acc | gat | gcg | gcg | gtt | caa | ttg | gta | gca | cat | gga | gcg | gat | 768 |
| Gln | Tyr | Leu | Thr | Asp | Ala | Ala | Val | Gln | Leu | Val | Ala | His | Gly | Ala | Asp | |
| | 210 | | | | | 215 | | | | | 220 | | | | | |
| ggt | ttg | cgg | att | gat | gcg | gtg | aag | cat | ttt | aat | tcg | ggg | ttc | tcc | aaa | 816 |

```
            Gly Leu Arg Ile Asp Ala Val Lys His Phe Asn Ser Gly Phe Ser Lys
                225                 230                 235 tcg ttg gcc gat aaa ctg tac caa aag aaa gac att ttc ctg gtg ggg        864
Ser Leu Ala Asp Lys Leu Tyr Gln Lys Lys Asp Ile Phe Leu Val Gly
240                 245                 250                 255 gaa tgg tac gga gat gac ccc gga aca gcc aat cat ctg gaa aag gtc        912
Glu Trp Tyr Gly Asp Asp Pro Gly Thr Ala Asn His Leu Glu Lys Val
                260                 265                 270 cgg tac gcc aac aac agc ggt gtc aat gtg ctg gat ttt gat ctc aac        960
Arg Tyr Ala Asn Asn Ser Gly Val Asn Val Leu Asp Phe Asp Leu Asn
                    275                 280                 285 acg gtg att cga aat gtg ttc ggc aca ttt acg caa acg atg tac gat       1008
Thr Val Ile Arg Asn Val Phe Gly Thr Phe Thr Gln Thr Met Tyr Asp
290                 295                 300 ctt aac aat atg gtg aac caa acg ggg aac gag tac aaa tac aaa gaa       1056
Leu Asn Asn Met Val Asn Gln Thr Gly Asn Glu Tyr Lys Tyr Lys Glu
                305                 310                 315 aat cta atc aca ttt atc gat aac cat gat atg tca aga ttt ctt tcg       1104
Asn Leu Ile Thr Phe Ile Asp Asn His Asp Met Ser Arg Phe Leu Ser
320                 325                 330                 335 gta aat tcg aac aag gcg aat ttg cac cag gcg ctt gct ttc att ctc       1152
Val Asn Ser Asn Lys Ala Asn Leu His Gln Ala Leu Ala Phe Ile Leu
                340                 345                 350 act tcg cgg ggt acg ccc tcc atc tat tat gga acc gaa caa tac atg       1200
Thr Ser Arg Gly Thr Pro Ser Ile Tyr Tyr Gly Thr Glu Gln Tyr Met
                355                 360                 365 gca ggc ggc aat gac ccg tac aac cgg ggg atg atg ccg gcg ttt gat       1248
Ala Gly Gly Asn Asp Pro Tyr Asn Arg Gly Met Met Pro Ala Phe Asp
                370                 375                 380 acg aca acc acc gcc ttt aaa gag gtg tca act ctg gcg ggg ttg cgc       1296
Thr Thr Thr Thr Ala Phe Lys Glu Val Ser Thr Leu Ala Gly Leu Arg
385                 390                 395 agg aac aat gcg gcg atc cag tac ggc acc acc acc cag cgt tgg atc       1344
Arg Asn Asn Ala Ala Ile Gln Tyr Gly Thr Thr Thr Gln Arg Trp Ile
400                 405                 410                 415 aac aat gat gtt tac att tat gaa cgg aaa ttt ttc aac gat gtc gtg       1392
Asn Asn Asp Val Tyr Ile Tyr Glu Arg Lys Phe Phe Asn Asp Val Val
                420                 425                 430 ttg gtg gcc atc aat cga aac acg caa tcc tcc tat tcg att tcc ggt       1440
Leu Val Ala Ile Asn Arg Asn Thr Gln Ser Ser Tyr Ser Ile Ser Gly
                435                 440                 445 ttg cag acg gcc ttg cca aat ggc agc tat gcg gat tat ctg tca ggg       1488
Leu Gln Thr Ala Leu Pro Asn Gly Ser Tyr Ala Asp Tyr Leu Ser Gly
        450                 455                 460 ctg ttg ggg ggg aac ggg att tcc gtt tcc aat gga agt gtc gct tcg       1536
Leu Leu Gly Gly Asn Gly Ile Ser Val Ser Asn Gly Ser Val Ala Ser
465                 470                 475 ttc acg ctt gcg cct gga gcc gtg tct gtt tgg cag tac agc aca tcc       1584
Phe Thr Leu Ala Pro Gly Ala Val Ser Val Trp Gln Tyr Ser Thr Ser
480                 485                 490                 495 gct tca gcg ccg caa atc gga tcg gtt gct cca aat atg ggg att ccg       1632
Ala Ser Ala Pro Gln Ile Gly Ser Val Ala Pro Asn Met Gly Ile Pro
                500                 505                 510 ggt aat gtg gtc acg atc gac ggg aaa ggt ttt ggg acg acg cag gga       1680
Gly Asn Val Val Thr Ile Asp Gly Lys Gly Phe Gly Thr Thr Gln Gly
                515                 520                 525 acc gtg aca ttt ggc gga gtg aca gcg act gtg aaa tcc tgg aca tcc       1728
Thr Val Thr Phe Gly Gly Val Thr Ala Thr Val Lys Ser Trp Thr Ser
                530                 535                 540
```

|  |  |
|---|---|
| aat cgg att gaa gtg tac gtt ccc aac atg gcc gcc ggg ctg acc gat<br>Asn Arg Ile Glu Val Tyr Val Pro Asn Met Ala Ala Gly Leu Thr Asp<br>545                  550                      555 | 1776 |
| gtg aaa gtc acc gcg ggt gga gtt tcc agc aat ctg tat tct tac aat<br>Val Lys Val Thr Ala Gly Gly Val Ser Ser Asn Leu Tyr Ser Tyr Asn<br>560                  565                    570                    575 | 1824 |
| att ttg agt gga acg cag aca tcg gtt gtg ttt act gtg aaa agt gcg<br>Ile Leu Ser Gly Thr Gln Thr Ser Val Val Phe Thr Val Lys Ser Ala<br>                  580                    585                    590 | 1872 |
| cct ccg acc aac ctg ggg gat aag att tac ctg acg ggc aac ata ccg<br>Pro Pro Thr Asn Leu Gly Asp Lys Ile Tyr Leu Thr Gly Asn Ile Pro<br>                  595                    600                    605 | 1920 |
| gaa ttg ggg aat tgg agc acg gat acg agc gga gcc gtt aac aat gcg<br>Glu Leu Gly Asn Trp Ser Thr Asp Thr Ser Gly Ala Val Asn Asn Ala<br>610                  615                    620 | 1968 |
| caa ggg ccc ctg ctc gcg ccc aat tat ccg gat tgg ttt tat gta ttc<br>Gln Gly Pro Leu Leu Ala Pro Asn Tyr Pro Asp Trp Phe Tyr Val Phe<br>625                  630                    635 | 2016 |
| agc gtt cca gca gga aag acg att caa ttc aag ttc ttc atc aag cgt<br>Ser Val Pro Ala Gly Lys Thr Ile Gln Phe Lys Phe Phe Ile Lys Arg<br>640                  645                    650                    655 | 2064 |
| gcg gat gga acg att caa tgg gag aat ggt tcg aac cac gtg gcc aca<br>Ala Asp Gly Thr Ile Gln Trp Glu Asn Gly Ser Asn His Val Ala Thr<br>                  660                    665                    670 | 2112 |
| act ccc acg ggt gca acc ggt aac att act gtt acg tgg caa aac tag<br>Thr Pro Thr Gly Ala Thr Gly Asn Ile Thr Val Thr Trp Gln Asn<br>                  675                    680                    685 | 2160 |

<210> SEQ ID NO 9
<211> LENGTH: 719
<212> TYPE: PRT
<213> ORGANISM: Bacillus sp.

<400> SEQUENCE: 9

Met Lys Lys Lys Thr Leu Ser Leu Phe Val Gly Leu Met Leu Leu Ile
            -30                    -25                    -20

Gly Leu Leu Phe Ser Gly Ser Leu Pro Tyr Asn Pro Asn Ala Ala Glu
     -15                    -10                    -5

Ala Ser Ser Ser Ala Ser Val Lys Gly Asp Val Ile Tyr Gln Ile Ile
-1  1             5                    10                    15

Ile Asp Arg Phe Tyr Asp Gly Asp Thr Thr Asn Asn Pro Ala Lys
              20                    25                    30

Ser Tyr Gly Leu Tyr Asp Pro Thr Lys Ser Lys Trp Lys Met Tyr Trp
         35                    40                    45

Gly Gly Asp Leu Glu Gly Val Arg Gln Lys Leu Pro Tyr Leu Lys Gln
     50                    55                    60

Leu Gly Val Thr Thr Ile Trp Leu Ser Pro Val Leu Asp Asn Leu Asp
65                  70                    75

Thr Leu Ala Gly Thr Asp Asn Thr Gly Tyr His Gly Tyr Trp Thr Arg
80                  85                    90                    95

Asp Phe Lys Gln Ile Glu Glu His Phe Gly Asn Trp Thr Thr Phe Asp
              100                    105                    110

Thr Leu Val Asn Asp Ala His Gln Asn Gly Ile Lys Val Ile Val Asp
         115                    120                    125

Phe Val Pro Asn His Ser Thr Pro Phe Lys Ala Asn Asp Ser Thr Phe
              130                    135                    140

Ala Glu Gly Gly Ala Leu Tyr Asn Asn Gly Thr Tyr Met Gly Asn Tyr
         145                    150                    155

```
Phe Asp Asp Ala Thr Lys Gly Tyr Phe His His Asn Gly Asp Ile Ser
160                 165                 170                 175

Asn Trp Asp Asp Arg Tyr Glu Ala Gln Trp Lys Asn Phe Thr Asp Pro
            180                 185                 190

Ala Gly Phe Ser Leu Ala Asp Leu Ser Gln Glu Asn Gly Thr Ile Ala
                195                 200                 205

Gln Tyr Leu Thr Asp Ala Ala Val Gln Leu Val Ala His Gly Ala Asp
            210                 215                 220

Gly Leu Arg Ile Asp Ala Val Lys His Phe Asn Ser Gly Phe Ser Lys
        225                 230                 235

Ser Leu Ala Asp Lys Leu Tyr Gln Lys Asp Ile Phe Leu Val Gly
240                 245                 250                 255

Glu Trp Tyr Gly Asp Asp Pro Gly Thr Ala Asn His Leu Glu Lys Val
                260                 265                 270

Arg Tyr Ala Asn Asn Ser Gly Val Asn Val Leu Asp Phe Asp Leu Asn
            275                 280                 285

Thr Val Ile Arg Asn Val Phe Gly Thr Phe Thr Gln Thr Met Tyr Asp
        290                 295                 300

Leu Asn Asn Met Val Asn Gln Thr Gly Asn Glu Tyr Lys Tyr Lys Glu
305                 310                 315

Asn Leu Ile Thr Phe Ile Asp Asn His Asp Met Ser Arg Phe Leu Ser
320                 325                 330                 335

Val Asn Ser Asn Lys Ala Asn Leu His Gln Ala Leu Ala Phe Ile Leu
            340                 345                 350

Thr Ser Arg Gly Thr Pro Ser Ile Tyr Tyr Gly Thr Glu Gln Tyr Met
        355                 360                 365

Ala Gly Gly Asn Asp Pro Tyr Asn Arg Gly Met Met Pro Ala Phe Asp
        370                 375                 380

Thr Thr Thr Thr Ala Phe Lys Glu Val Ser Thr Leu Ala Gly Leu Arg
385                 390                 395

Arg Asn Asn Ala Ala Ile Gln Tyr Gly Thr Thr Thr Gln Arg Trp Ile
400                 405                 410                 415

Asn Asn Asp Val Tyr Ile Tyr Glu Arg Lys Phe Phe Asn Asp Val Val
            420                 425                 430

Leu Val Ala Ile Asn Arg Asn Thr Gln Ser Ser Tyr Ser Ile Ser Gly
            435                 440                 445

Leu Gln Thr Ala Leu Pro Asn Gly Ser Tyr Ala Asp Tyr Leu Ser Gly
        450                 455                 460

Leu Leu Gly Gly Asn Gly Ile Ser Val Ser Asn Gly Ser Val Ala Ser
        465                 470                 475

Phe Thr Leu Ala Pro Gly Ala Val Ser Val Trp Gln Tyr Ser Thr Ser
480                 485                 490                 495

Ala Ser Ala Pro Gln Ile Gly Ser Val Ala Pro Asn Met Gly Ile Pro
            500                 505                 510

Gly Asn Val Val Thr Ile Asp Gly Lys Gly Phe Gly Thr Thr Gln Gly
            515                 520                 525

Thr Val Thr Phe Gly Gly Val Thr Ala Thr Val Lys Ser Trp Thr Ser
        530                 535                 540

Asn Arg Ile Glu Val Tyr Val Pro Asn Met Ala Ala Gly Leu Thr Asp
        545                 550                 555

Val Lys Val Thr Ala Gly Gly Val Ser Ser Asn Leu Tyr Ser Tyr Asn
560                 565                 570                 575
```

```
Ile Leu Ser Gly Thr Gln Thr Ser Val Val Phe Thr Val Lys Ser Ala
                    580                 585                 590

Pro Pro Thr Asn Leu Gly Asp Lys Ile Tyr Leu Thr Gly Asn Ile Pro
            595                 600                 605

Glu Leu Gly Asn Trp Ser Thr Asp Thr Ser Gly Ala Val Asn Asn Ala
            610                 615                 620

Gln Gly Pro Leu Leu Ala Pro Asn Tyr Pro Asp Trp Phe Tyr Val Phe
        625                 630                 635

Ser Val Pro Ala Gly Lys Thr Ile Gln Phe Lys Phe Ile Lys Arg
640                 645                 650                 655

Ala Asp Gly Thr Ile Gln Trp Glu Asn Gly Ser Asn His Val Ala Thr
                660                 665                 670

Thr Pro Thr Gly Ala Thr Gly Asn Ile Thr Val Thr Trp Gln Asn
            675                 680                 685

<210> SEQ ID NO 10
<211> LENGTH: 514
<212> TYPE: PRT
<213> ORGANISM: Bacillus stearothermophilus
<220> FEATURE:
<221> NAME/KEY: mat_peptide
<222> LOCATION: (1)..(514)

<400> SEQUENCE: 10

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255
```

-continued

```
Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 11
<211> LENGTH: 484
<212> TYPE: PRT
<213> ORGANISM: Aspergillus niger
<220> FEATURE:
<221> NAME/KEY: mat_peptide
<222> LOCATION: (1)..(484)

<400> SEQUENCE: 11

Leu Ser Ala Ala Ser Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asn Glu Ile Tyr Cys Gly Gly Ser Trp Gln Gly Ile Ile Asp His
        35                  40                  45

Leu Asp Tyr Ile Glu Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
                85                  90                  95
```

```
Ala Asp Asn Leu Lys Ser Leu Ser Asp Ala Leu His Ala Arg Gly Met
            100                 105                 110

Tyr Leu Met Val Asp Val Val Pro Asp His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Glu Asp Cys Trp Glu Gly Asp Thr Ile Val Ser Leu Pro Asp Leu
                165                 170                 175

Asp Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Leu Glu Val Gln Pro Asp Phe Phe Pro Gly Tyr Asn Lys Ala Ser Gly
    210                 215                 220

Val Tyr Cys Val Gly Glu Ile Asp Asn Gly Asn Pro Ala Ser Asp Cys
225                 230                 235                 240

Pro Tyr Gln Lys Val Leu Asp Gly Val Leu Asn Tyr Pro Ile Tyr Trp
                245                 250                 255

Gln Leu Leu Tyr Ala Phe Glu Ser Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Lys Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Gln His Tyr Ala
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ala Ala Asp Ser Ala Tyr Ile Thr Tyr Ala Asn
370                 375                 380

Asp Ala Phe Tyr Thr Asp Ser Asn Thr Ile Ala Met Ala Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Ser
        435                 440                 445

Gly Asp Ile Pro Val Pro Met Ala Ser Gly Leu Pro Arg Val Leu Leu
    450                 455                 460

Pro Ala Ser Val Val Asp Ser Ser Ser Leu Cys Gly Gly Ser Gly Arg
465                 470                 475                 480

Leu Tyr Val Glu

<210> SEQ ID NO 12
<211> LENGTH: 435
<212> TYPE: PRT
```

```
<213> ORGANISM: Humicola insolens
<220> FEATURE:
<221> NAME/KEY: mat_peptide
<222> LOCATION: (1)..(435)

<400> SEQUENCE: 12

Met Ala Arg Gly Thr Ala Leu Leu Gly Leu Thr Ala Leu Leu Leu Gly
1               5                   10                  15

Leu Val Asn Gly Gln Lys Pro Gly Glu Thr Lys Glu Val His Pro Gln
            20                  25                  30

Leu Thr Thr Phe Arg Cys Thr Lys Arg Gly Gly Cys Lys Pro Ala Thr
        35                  40                  45

Asn Phe Ile Val Leu Asp Ser Leu Ser His Pro Ile His Arg Ala Glu
    50                  55                  60

Gly Leu Gly Pro Gly Gly Cys Gly Asp Trp Gly Asn Pro Pro Lys
65                  70                  75                  80

Asp Val Cys Pro Asp Val Glu Ser Cys Ala Lys Asn Cys Ile Met Glu
                85                  90                  95

Gly Ile Pro Asp Tyr Ser Gln Tyr Gly Val Thr Thr Asn Gly Thr Ser
            100                 105                 110

Leu Arg Leu Gln His Ile Leu Pro Asp Gly Arg Val Pro Ser Pro Arg
        115                 120                 125

Val Tyr Leu Leu Asp Lys Thr Lys Arg Arg Tyr Glu Met Leu His Leu
    130                 135                 140

Thr Gly Phe Glu Phe Thr Phe Asp Val Asp Ala Thr Lys Leu Pro Cys
145                 150                 155                 160

Gly Met Asn Ser Ala Leu Tyr Leu Ser Glu Met His Pro Thr Gly Ala
                165                 170                 175

Lys Ser Lys Tyr Asn Ser Gly Gly Ala Tyr Tyr Gly Thr Gly Tyr Cys
            180                 185                 190

Asp Ala Gln Cys Phe Val Thr Pro Phe Ile Asn Gly Leu Gly Asn Ile
        195                 200                 205

Glu Gly Lys Gly Ser Cys Cys Asn Glu Met Asp Ile Trp Glu Val Asn
    210                 215                 220

Ser Arg Ala Ser His Val Val Pro His Thr Cys Asn Lys Lys Gly Leu
225                 230                 235                 240

Tyr Leu Cys Glu Gly Glu Glu Cys Ala Phe Glu Gly Val Cys Asp Lys
                245                 250                 255

Asn Gly Cys Gly Trp Asn Asn Tyr Arg Val Asn Val Thr Asp Tyr Tyr
            260                 265                 270

Gly Arg Gly Glu Glu Phe Lys Val Asn Thr Leu Lys Pro Phe Thr Val
        275                 280                 285

Val Thr Gln Phe Leu Ala Asn Arg Arg Gly Lys Leu Glu Lys Ile His
    290                 295                 300

Arg Phe Tyr Val Gln Asp Gly Lys Val Ile Glu Ser Phe Tyr Thr Asn
305                 310                 315                 320

Lys Glu Gly Val Pro Tyr Thr Asn Met Ile Asp Asp Glu Phe Cys Glu
                325                 330                 335

Ala Thr Gly Ser Arg Lys Tyr Met Glu Leu Gly Ala Thr Gln Gly Met
            340                 345                 350

Gly Glu Ala Leu Thr Arg Gly Met Val Leu Ala Met Ser Ile Trp Trp
        355                 360                 365

Asp Gln Gly Gly Asn Met Glu Trp Leu Asp His Gly Glu Ala Gly Pro
    370                 375                 380
```

-continued

```
Cys Ala Lys Gly Glu Gly Ala Pro Ser Asn Ile Val Gln Val Glu Pro
385                 390                 395                 400

Phe Pro Glu Val Thr Tyr Thr Asn Leu Arg Trp Gly Glu Ile Gly Ser
                405                 410                 415

Thr Tyr Gln Glu Val Gln Lys Pro Lys Pro Lys Pro Gly His Gly Pro
            420                 425                 430

Arg Ser Asp
        435

<210> SEQ ID NO 13
<211> LENGTH: 1008
<212> TYPE: DNA
<213> ORGANISM: Thermoascus aurantiacus
<220> FEATURE:
<221> NAME/KEY: CDS
<222> LOCATION: (1)..(1005)
<220> FEATURE:
<221> NAME/KEY: sig_peptide
<222> LOCATION: (1)..(90)
<220> FEATURE:
<221> NAME/KEY: mat_peptide
<222> LOCATION: (91)..(1005)

<400> SEQUENCE: 13
```

```
atg aag ctc ggc tct ctc gtg ctc gct ctc agc gca gct agg ctt aca      48
Met Lys Leu Gly Ser Leu Val Leu Ala Leu Ser Ala Ala Arg Leu Thr
-30             -25                 -20                 -15 ctg tcg gcc cct ctc gca gac aga aag cag gag acc aag cgt gcg aaa      96
Leu Ser Ala Pro Leu Ala Asp Arg Lys Gln Glu Thr Lys Arg Ala Lys
            -10                 -5                  -1   1 gta ttc caa tgg ttc ggt tcg aac gag tcc ggt gct gaa ttc gga agc     144
Val Phe Gln Trp Phe Gly Ser Asn Glu Ser Gly Ala Glu Phe Gly Ser
        5                   10                  15 cag aac ctt cca gga gtc gag gga aag gat tat ata tgg cct gat ccc     192
Gln Asn Leu Pro Gly Val Glu Gly Lys Asp Tyr Ile Trp Pro Asp Pro
    20                  25                  30 aac acc att gac aca ttg atc agc aag ggg atg aac atc ttt cgt gtc     240
Asn Thr Ile Asp Thr Leu Ile Ser Lys Gly Met Asn Ile Phe Arg Val
35                  40                  45                  50 ccc ttt atg atg gag aga ttg gtt ccc aac tca atg acc ggc tct ccg     288
Pro Phe Met Met Glu Arg Leu Val Pro Asn Ser Met Thr Gly Ser Pro
                55                  60                  65 gat ccg aac tac ctg gca gat ctc ata gcg act gta aat gca atc acc     336
Asp Pro Asn Tyr Leu Ala Asp Leu Ile Ala Thr Val Asn Ala Ile Thr
            70                  75                  80 cag aaa ggt gcc tac gcc gtc gtc gat cct cat aac tac ggc aga tac     384
Gln Lys Gly Ala Tyr Ala Val Val Asp Pro His Asn Tyr Gly Arg Tyr
        85                  90                  95 tac aat tct ata atc tcg agc cct tcc gat ttc cag acc ttc tgg aaa     432
Tyr Asn Ser Ile Ile Ser Ser Pro Ser Asp Phe Gln Thr Phe Trp Lys
    100                 105                 110 acg gtc gcc tca cag ttt gct tcg aat cca ctg gtc atc ttc gac act     480
Thr Val Ala Ser Gln Phe Ala Ser Asn Pro Leu Val Ile Phe Asp Thr
115                 120                 125                 130 aat aac gaa tac cac gat atg gac cag acc tta gtc ctc aat ctc aac     528
Asn Asn Glu Tyr His Asp Met Asp Gln Thr Leu Val Leu Asn Leu Asn
                135                 140                 145 cag gcc gct atc gac ggc atc cgt tcc gcc gga gcc act tcc cag tac     576
Gln Ala Ala Ile Asp Gly Ile Arg Ser Ala Gly Ala Thr Ser Gln Tyr
            150                 155                 160 atc ttt gtc gag ggc aat tcg tgg acc ggg gca tgg acc tgg acg aac     624
Ile Phe Val Glu Gly Asn Ser Trp Thr Gly Ala Trp Thr Trp Thr Asn
```

```
                    165                 170                 175
gtg aac gat aac atg aaa agc ctg acc gac cca tct gac aag atc ata      672
Val Asn Asp Asn Met Lys Ser Leu Thr Asp Pro Ser Asp Lys Ile Ile
    180                 185                 190 tac gag atg cac cag tac ctg gac tct gac gga tcc ggg aca tca gcg      720
Tyr Glu Met His Gln Tyr Leu Asp Ser Asp Gly Ser Gly Thr Ser Ala
195                 200                 205                 210 acc tgc gta tct tcg acc atc ggt caa gag cga atc acc agc gca acg      768
Thr Cys Val Ser Ser Thr Ile Gly Gln Glu Arg Ile Thr Ser Ala Thr
                215                 220                 225 cag tgg ctc agg gcc aac ggg aag aag ggc atc atc ggc gag ttt gcg      816
Gln Trp Leu Arg Ala Asn Gly Lys Lys Gly Ile Ile Gly Glu Phe Ala
            230                 235                 240 ggc gga gcc aac gac gtc tgc gag acg gcc atc acg ggc atg ctg gac      864
Gly Gly Ala Asn Asp Val Cys Glu Thr Ala Ile Thr Gly Met Leu Asp
        245                 250                 255 tac atg gcc cag aac aca gac gtc tgg act ggc gcc atc tgg tgg gcg      912
Tyr Met Ala Gln Asn Thr Asp Val Trp Thr Gly Ala Ile Trp Trp Ala
    260                 265                 270 gcc ggg ccg tgg tgg gga gac tac ata ttc tcc atg gag ccg gac aat      960
Ala Gly Pro Trp Trp Gly Asp Tyr Ile Phe Ser Met Glu Pro Asp Asn
275                 280                 285                 290 ggc atc gcg tat cag cag ata ctt cct att ttg act ccg tat ctt tga    1008
Gly Ile Ala Tyr Gln Gln Ile Leu Pro Ile Leu Thr Pro Tyr Leu
                295                 300                 305

<210> SEQ ID NO 14
<211> LENGTH: 335
<212> TYPE: PRT
<213> ORGANISM: Thermoascus aurantiacus

<400> SEQUENCE: 14

Met Lys Leu Gly Ser Leu Val Leu Ala Leu Ser Ala Ala Arg Leu Thr
-30                 -25                 -20                 -15

Leu Ser Ala Pro Leu Ala Asp Arg Lys Gln Glu Thr Lys Arg Ala Lys
            -10                 -5                  -1   1

Val Phe Gln Trp Phe Gly Ser Asn Glu Ser Gly Ala Glu Phe Gly Ser
        5                   10                  15

Gln Asn Leu Pro Gly Val Glu Gly Lys Asp Tyr Ile Trp Pro Asp Pro
    20                  25                  30

Asn Thr Ile Asp Thr Leu Ile Ser Lys Gly Met Asn Ile Phe Arg Val
35                  40                  45                  50

Pro Phe Met Met Glu Arg Leu Val Pro Asn Ser Met Thr Gly Ser Pro
                55                  60                  65

Asp Pro Asn Tyr Leu Ala Asp Leu Ile Ala Thr Val Asn Ala Ile Thr
            70                  75                  80

Gln Lys Gly Ala Tyr Ala Val Val Asp Pro His Asn Tyr Gly Arg Tyr
        85                  90                  95

Tyr Asn Ser Ile Ile Ser Ser Pro Ser Asp Phe Gln Thr Phe Trp Lys
    100                 105                 110

Thr Val Ala Ser Gln Phe Ala Ser Asn Pro Leu Val Ile Phe Asp Thr
115                 120                 125                 130

Asn Asn Glu Tyr His Asp Met Asp Gln Thr Leu Val Leu Asn Leu Asn
                135                 140                 145

Gln Ala Ala Ile Asp Gly Ile Arg Ser Ala Gly Ala Thr Ser Gln Tyr
            150                 155                 160

Ile Phe Val Glu Gly Asn Ser Trp Thr Gly Ala Trp Thr Trp Thr Asn
```

-continued

```
            165                 170                 175
Val Asn Asp Asn Met Lys Ser Leu Thr Asp Pro Ser Asp Lys Ile Ile
        180                 185                 190

Tyr Glu Met His Gln Tyr Leu Asp Ser Asp Gly Ser Gly Thr Ser Ala
195                 200                 205                 210

Thr Cys Val Ser Ser Thr Ile Gly Gln Glu Arg Ile Thr Ser Ala Thr
                215                 220                 225

Gln Trp Leu Arg Ala Asn Gly Lys Lys Gly Ile Ile Gly Glu Phe Ala
            230                 235                 240

Gly Gly Ala Asn Asp Val Cys Glu Thr Ala Ile Thr Gly Met Leu Asp
            245                 250                 255

Tyr Met Ala Gln Asn Thr Asp Val Trp Thr Gly Ala Ile Trp Trp Ala
        260                 265                 270

Ala Gly Pro Trp Trp Gly Asp Tyr Ile Phe Ser Met Glu Pro Asp Asn
275                 280                 285                 290

Gly Ile Ala Tyr Gln Gln Ile Leu Pro Ile Leu Thr Pro Tyr Leu
                295                 300                 305
```